US012378543B2

(12) United States Patent
George et al.

(10) Patent No.: US 12,378,543 B2
(45) Date of Patent: Aug. 5, 2025

(54) COMPOSITIONS FOR HEMOLYSIS AND COAGULATION REGULATION AND STABILIZATION OF EXTRACELLULAR VESICLES

(71) Applicant: STRECK LLC, La Vista, NE (US)

(72) Inventors: Nicholas Michael George, Omaha, NE (US); Bradford A. Hunsley, Papillion, NE (US)

(73) Assignee: STRECK LLC, La Vista, NE (US)

( * ) Notice: Subject to any disclaimer, the term of this patent is extended or adjusted under 35 U.S.C. 154(b) by 336 days.

(21) Appl. No.: 16/756,803

(22) PCT Filed: Oct. 19, 2018

(86) PCT No.: PCT/US2018/056747
§ 371 (c)(1),
(2) Date: Apr. 16, 2020

(87) PCT Pub. No.: WO2019/079743
PCT Pub. Date: Apr. 25, 2019

(65) Prior Publication Data
US 2021/0371848 A1 Dec. 2, 2021

Related U.S. Application Data

(60) Provisional application No. 62/574,515, filed on Oct. 19, 2017.

(51) Int. Cl.
C12N 15/10 (2006.01)
A01N 1/124 (2025.01)
A01N 1/126 (2025.01)

(52) U.S. Cl.
CPC ......... *C12N 15/1003* (2013.01); *A01N 1/124* (2025.01); *A01N 1/126* (2025.01)

(58) Field of Classification Search
CPC ................................................... A01N 1/0226
USPC ........................................................ 536/254
See application file for complete search history.

(56) References Cited

U.S. PATENT DOCUMENTS

| | | |
|---|---|---|
| 1,432,249 A | 10/1922 | Hoyme |
| 1,922,799 A | 8/1933 | Gaus |
| 2,250,666 A | 7/1941 | Webb |
| 2,690,624 A | 10/1954 | Phillips |
| 2,930,570 A | 3/1960 | Leedy |
| 3,781,120 A | 12/1973 | Engelhardt |
| 3,867,521 A | 2/1975 | Miskel et al. |
| 3,872,730 A | 3/1975 | Ringrose et al. |
| 3,874,384 A | 4/1975 | Deindoerfer et al. |
| 3,879,295 A | 4/1975 | Glover et al. |
| 3,973,913 A | 8/1976 | Louderback |
| 3,994,085 A | 11/1976 | Groselak et al. |
| 4,043,453 A | 8/1977 | Greenlee |
| 4,318,090 A | 3/1982 | Narlow et al. |
| 4,436,821 A | 3/1984 | Ryan |
| 4,513,522 A | 4/1985 | Selenke |
| 4,515,890 A | 5/1985 | Manderino et al. |
| 4,579,759 A | 4/1986 | Breuers |
| 4,584,219 A | 4/1986 | Baartmans |
| 4,675,159 A | 6/1987 | Al-Sioufi |
| 4,818,700 A | 4/1989 | Cregg et al. |
| 4,884,827 A | 12/1989 | Kelley |
| 4,921,277 A | 5/1990 | McDonough |
| 5,000,484 A | 3/1991 | Phelan et al. |
| 5,060,672 A | 10/1991 | Irimi et al. |
| 5,110,908 A | 5/1992 | Deich et al. |
| 5,135,125 A | 8/1992 | Andel et al. |
| 5,196,182 A | 3/1993 | Ryan |
| 5,213,765 A | 5/1993 | Kasai et al. |
| 5,250,438 A | 10/1993 | Ryan |
| 5,257,633 A | 11/1993 | Vogler et al. |
| 5,260,048 A | 11/1993 | Ryan |
| 5,270,208 A | 12/1993 | Ryan |
| 5,343,647 A | 9/1994 | Bulka |
| 5,366,249 A | 11/1994 | Diemert |
| 5,429,797 A | 7/1995 | Camiener |
| 5,447,842 A | 9/1995 | Simons |
| 5,457,024 A | 10/1995 | Goldbard |
| 5,459,073 A | 10/1995 | Ryan |
| 5,459,253 A | 10/1995 | Wolin et al. |
| 5,460,797 A | 10/1995 | Ryan |
| 5,468,022 A | 11/1995 | Linder et al. |
| 5,490,658 A | 2/1996 | Coward et al. |
| 5,501,954 A | 3/1996 | Mahr et al. |
| 5,501,963 A | 3/1996 | Burckhardt |
| 5,512,343 A | 4/1996 | Shaw |
| 5,538,871 A | 7/1996 | Nuovo et al. |
| 5,540,358 A | 7/1996 | Wiles et al. |
| 5,560,657 A | 10/1996 | Morgan |
| 5,614,391 A | 3/1997 | Franciskovich et al. |
| 5,618,664 A | 4/1997 | Kiessling |
| 5,629,147 A | 5/1997 | Asgari et al. |
| D382,343 S | 8/1997 | Wandell et al. |
| 5,654,054 A | 8/1997 | Tropsha et al. |
| 5,688,516 A | 11/1997 | Raad et al. |
| 5,731,156 A | 3/1998 | Golbus |
| 5,741,638 A | 4/1998 | Yamane |
| 5,783,093 A | 7/1998 | Holme |

(Continued)

FOREIGN PATENT DOCUMENTS

| | | |
|---|---|---|
| AU | 2008288601 A1 | 4/2009 |
| CA | 2406463 A1 | 11/2001 |

(Continued)

OTHER PUBLICATIONS

Koba et al., Postepy High Med Dosw, 2005, 59, 290-8-English Abstract.*

(Continued)

*Primary Examiner* — Ganapathy Krishnan
(74) *Attorney, Agent, or Firm* — MARSHALL, GERSTEIN & BORUN LLP

(57) ABSTRACT

A composition and method of use thereof wherein the composition comprises one or more components capable of releasing an aldehyde, one or more anticoagulants or chelating agents, and one or more polysaccharides. The composition has a pH of from about 4 to about 6.

17 Claims, 10 Drawing Sheets

(56) References Cited

U.S. PATENT DOCUMENTS

| | | |
|---|---|---|
| 5,811,099 A | 9/1998 | Ryan |
| 5,817,519 A | 10/1998 | Zelmanovic et al. |
| 5,849,517 A | 12/1998 | Ryan |
| 5,858,699 A | 1/1999 | Granger et al. |
| 5,861,253 A | 1/1999 | Asgari et al. |
| 5,888,822 A | 3/1999 | Hengstenberg |
| 5,906,744 A | 5/1999 | Carroll et al. |
| 5,939,259 A | 8/1999 | Harvey et al. |
| 5,962,234 A | 10/1999 | Golbus |
| 5,976,014 A | 11/1999 | Petrick et al. |
| 5,977,153 A | 11/1999 | Camiener |
| 5,985,572 A | 11/1999 | MacFarlane |
| 6,013,240 A | 1/2000 | Behr et al. |
| 6,030,767 A | 2/2000 | Wagner et al. |
| 6,043,032 A | 3/2000 | Yamagishi |
| 6,072,086 A | 6/2000 | James et al. |
| 6,074,825 A | 6/2000 | Rundell et al. |
| 6,074,827 A | 6/2000 | Nelson et al. |
| 6,077,235 A | 6/2000 | Serpentino et al. |
| 6,125,563 A | 10/2000 | Girerd |
| 6,128,840 A | 10/2000 | Boisvert |
| 6,168,922 B1 | 1/2001 | Harvey et al. |
| 6,177,163 B1 | 1/2001 | Blok et al. |
| 6,190,609 B1 | 2/2001 | Chapman et al. |
| 6,197,539 B1 | 3/2001 | Granger et al. |
| 6,197,540 B1 | 3/2001 | Granger et al. |
| 6,200,500 B1 | 3/2001 | Ryan |
| 6,210,889 B1 | 4/2001 | Drouin et al. |
| 6,218,531 B1 | 4/2001 | Ekenberg |
| 6,221,668 B1 | 4/2001 | Ryan et al. |
| 6,251,638 B1 | 6/2001 | Umansky et al. |
| 6,258,540 B1 | 7/2001 | Lo et al. |
| 6,287,820 B1 | 9/2001 | Umansky et al. |
| 6,337,189 B1 | 1/2002 | Ryan |
| 6,365,362 B1 | 4/2002 | Terstappen et al. |
| 6,399,388 B1 | 6/2002 | Ryan et al. |
| 6,403,377 B1 | 6/2002 | Ryan et al. |
| 6,406,915 B2 | 6/2002 | Ryan et al. |
| 6,527,242 B1 | 3/2003 | Kennedy |
| 6,527,957 B1 | 3/2003 | Deniega et al. |
| 6,551,267 B1 | 4/2003 | Cohen et al. |
| 6,560,847 B2 | 5/2003 | Ohlsson |
| 6,579,672 B1 | 6/2003 | Granger et al. |
| 6,581,973 B2 | 6/2003 | Levine et al. |
| 6,602,718 B1 | 8/2003 | Augello et al. |
| 6,617,170 B2 | 9/2003 | Augello et al. |
| 6,617,180 B1 | 9/2003 | Wang |
| 6,623,983 B1 | 9/2003 | Terstappen et al. |
| 6,630,301 B1 | 10/2003 | Gocke et al. |
| 6,645,731 B2 | 11/2003 | Terstappen et al. |
| 6,664,056 B2 | 12/2003 | Lo et al. |
| 6,759,217 B2 | 7/2004 | Kopreski |
| 6,821,789 B2 | 11/2004 | Augello et al. |
| 6,860,513 B2 | 3/2005 | Kaufman |
| 6,884,573 B2 | 4/2005 | Fischer et al. |
| 6,913,932 B2 | 7/2005 | Maples et al. |
| 6,916,634 B2 | 7/2005 | Kopreski |
| 6,939,671 B2 | 9/2005 | Kopreski |
| 6,994,790 B2 | 2/2006 | Corbin et al. |
| 7,022,478 B2 | 4/2006 | Rainer et al. |
| 7,044,941 B2 | 5/2006 | Mathias et al. |
| 7,208,275 B2 | 4/2007 | Gocke et al. |
| 7,267,980 B1 | 9/2007 | Mortari et al. |
| 7,282,371 B2 | 10/2007 | Helftenbein |
| 7,288,380 B1 | 10/2007 | Gocke et al. |
| 7,318,293 B2 | 1/2008 | Ardern, II |
| 7,332,277 B2 | 2/2008 | Dhallan |
| 7,332,288 B2 | 2/2008 | Terstappen et al. |
| 7,358,039 B2 | 4/2008 | Fischer et al. |
| 7,390,663 B2 | 6/2008 | Ryan et al. |
| 7,398,999 B2 | 7/2008 | Kaufman |
| 7,419,832 B2 | 9/2008 | Hunsley et al. |
| 7,442,506 B2 | 10/2008 | Dhallan |
| 7,445,901 B2 | 11/2008 | Kudlicki et al. |
| 7,478,513 B2 | 1/2009 | Baldwin |
| 7,569,350 B2 | 8/2009 | Gocke et al. |
| 7,651,838 B2 | 1/2010 | Paterlini-Brechot |
| 7,727,720 B2 | 6/2010 | Dhallan |
| 7,767,460 B2 | 8/2010 | Hunsley et al. |
| 8,304,187 B2 | 11/2012 | Fernando |
| 8,546,144 B2 | 10/2013 | Das et al. |
| 8,551,784 B2 | 10/2013 | Das et al. |
| 8,586,306 B2 | 11/2013 | Fernando |
| 8,841,077 B2 | 9/2014 | Paige et al. |
| 9,034,635 B2 | 5/2015 | Termaat et al. |
| 9,040,255 B2 | 5/2015 | Tsinberg et al. |
| 9,120,840 B2 | 9/2015 | Janssen et al. |
| 9,120,849 B2 | 9/2015 | Chiklis et al. |
| 9,127,048 B2 | 9/2015 | Chiklis et al. |
| 9,127,049 B2 | 9/2015 | MacAgno et al. |
| 9,657,227 B2 | 5/2017 | Fernando |
| 9,926,590 B2 | 3/2018 | Fernando |
| 9,926,950 B2 | 3/2018 | Ooki et al. |
| 9,956,281 B2 | 5/2018 | Ryan et al. |
| 10,006,861 B2 | 6/2018 | Kreifels et al. |
| 10,091,984 B2 | 10/2018 | Fernando et al. |
| 10,144,955 B2 | 12/2018 | Fernando |
| 10,294,513 B2 | 5/2019 | Fernando |
| 11,168,351 B2 | 11/2021 | Hunsley et al. |
| 2001/0018192 A1 | 8/2001 | Terstappen et al. |
| 2001/0049895 A1 | 12/2001 | Burke |
| 2001/0051341 A1 | 12/2001 | Lo et al. |
| 2002/0045196 A1 | 4/2002 | Mahoney et al. |
| 2002/0066216 A1 | 6/2002 | Delacruz |
| 2002/0086346 A1 | 7/2002 | Ryan |
| 2002/0119503 A1 | 8/2002 | Ryan et al. |
| 2003/0113705 A1 | 6/2003 | McMillian |
| 2003/0232377 A1 | 12/2003 | Thomas |
| 2004/0014107 A1 | 1/2004 | Garcia-Blanco et al. |
| 2004/0038424 A1 | 2/2004 | Maples |
| 2004/0137417 A1 | 7/2004 | Ryan |
| 2005/0029559 A9 | 2/2005 | Ahn et al. |
| 2005/0049793 A1 | 3/2005 | Paterlini-Brechot |
| 2005/0107316 A1 | 5/2005 | Strebhardt et al. |
| 2005/0164241 A1 | 7/2005 | Hahn et al. |
| 2005/0181353 A1 | 8/2005 | Rao et al. |
| 2005/0181463 A1 | 8/2005 | Rao et al. |
| 2005/0232377 A1 | 10/2005 | Kutz et al. |
| 2005/0277204 A1 | 12/2005 | Hollis et al. |
| 2006/0008807 A1 | 1/2006 | O'Hara et al. |
| 2006/0105372 A1 | 5/2006 | Bair et al. |
| 2006/0194192 A1 | 8/2006 | Rao et al. |
| 2006/0210429 A1 | 9/2006 | Hunsley et al. |
| 2007/0111233 A1 | 5/2007 | Bianchi et al. |
| 2007/0134658 A1 | 6/2007 | Bohmer |
| 2007/0178478 A1 | 8/2007 | Dhallan et al. |
| 2007/0202525 A1 | 8/2007 | Quake et al. |
| 2007/0243548 A1 | 10/2007 | Georges et al. |
| 2007/0243549 A1 | 10/2007 | Bischoff |
| 2007/0251337 A1 | 11/2007 | Reed et al. |
| 2007/0298406 A1 | 12/2007 | Martorell et al. |
| 2008/0020390 A1 | 1/2008 | Mitchell et al. |
| 2008/0057502 A1 | 3/2008 | Kopreski |
| 2008/0081689 A1 | 4/2008 | Seelig et al. |
| 2008/0096217 A1 | 4/2008 | Kopreski |
| 2008/0102470 A1 | 5/2008 | Dawson et al. |
| 2008/0108071 A1 | 5/2008 | Thompson |
| 2008/0119645 A1 | 5/2008 | Griffey et al. |
| 2008/0206866 A1 | 8/2008 | Zieglschmid et al. |
| 2008/0261292 A1 | 10/2008 | Kopreski |
| 2008/0318801 A1 | 12/2008 | Leung |
| 2009/0011043 A1 | 1/2009 | Xie |
| 2009/0034446 A1 | 2/2009 | Adams et al. |
| 2009/0081678 A1 | 3/2009 | Ryan et al. |
| 2009/0197275 A1 | 8/2009 | Boonyarantanakornkit et al. |
| 2009/0215036 A1 | 8/2009 | Stropp et al. |
| 2009/0308303 A1 | 12/2009 | Burlando |
| 2010/0167271 A1 | 7/2010 | Ryan |
| 2010/0184069 A1 | 7/2010 | Fernando et al. |
| 2010/0190796 A1 | 7/2010 | Verkman et al. |
| 2010/0209930 A1 | 8/2010 | Fernando |
| 2010/0216153 A1 | 8/2010 | Lapidus et al. |
| 2010/0317107 A1 | 12/2010 | Ryan |

(56) References Cited

U.S. PATENT DOCUMENTS

| | | | |
|---|---|---|---|
| 2011/0027771 A1* | 2/2011 | Deng | G01N 33/80 |
| | | | 435/5 |
| 2011/0053208 A1 | 3/2011 | Reiss et al. | |
| 2011/0110975 A1 | 5/2011 | Grunkemeyer et al. | |
| 2011/0111410 A1 | 5/2011 | Ryan et al. | |
| 2011/0275536 A1 | 11/2011 | Kas | |
| 2012/0028236 A1 | 2/2012 | Sehgal | |
| 2012/0164676 A1 | 6/2012 | Tsinberg et al. | |
| 2012/0308990 A1 | 12/2012 | Termaat et al. | |
| 2013/0034860 A1 | 2/2013 | Fernando | |
| 2013/0183661 A1 | 7/2013 | Prante et al. | |
| 2013/0209985 A1 | 8/2013 | Dudaronek et al. | |
| 2014/0044752 A1 | 2/2014 | Ryan et al. | |
| 2014/0054508 A1 | 2/2014 | Fernando | |
| 2014/0080112 A1 | 3/2014 | Ryan et al. | |
| 2014/0199681 A1 | 7/2014 | Ryan et al. | |
| 2014/0274740 A1 | 9/2014 | Srinivasan et al. | |
| 2015/0030578 A1 | 1/2015 | Releford et al. | |
| 2015/0301037 A1 | 10/2015 | Tsinberg et al. | |
| 2016/0143268 A1 | 5/2016 | Ryan | |
| 2016/0174544 A1 | 6/2016 | Fernando et al. | |
| 2016/0257995 A1 | 9/2016 | Hunsley et al. | |
| 2017/0052173 A1 | 2/2017 | Hunsley et al. | |
| 2017/0097361 A1 | 4/2017 | Alt et al. | |
| 2017/0145475 A1* | 5/2017 | Hunsley | C12Q 1/6806 |
| 2018/0243406 A1 | 8/2018 | Ryan et al. | |
| 2019/0127780 A1 | 5/2019 | Hunsley et al. | |
| 2019/0177774 A1 | 6/2019 | Connelly et al. | |
| 2021/0031012 A1 | 2/2021 | Jones et al. | |
| 2021/0310045 A1 | 10/2021 | Kmper et al. | |

FOREIGN PATENT DOCUMENTS

| | | |
|---|---|---|
| CN | 1665554 A | 9/2005 |
| CN | 101148658 A | 3/2008 |
| CN | 104070871 A | 10/2014 |
| CN | 104381245 A | 3/2015 |
| CN | 104634628 A | 5/2015 |
| CN | 105985904 A | 10/2016 |
| CN | 107525818 A | 12/2017 |
| DE | 19928820 A1 | 12/2000 |
| EP | 1031626 A1 | 8/2000 |
| EP | 1207208 A2 | 5/2002 |
| EP | 1212613 A1 | 6/2002 |
| EP | 1217372 A1 | 6/2002 |
| EP | 1425294 A2 | 6/2004 |
| EP | 1816461 A1 | 8/2007 |
| EP | 1889921 A2 | 2/2008 |
| EP | 2216416 A1 | 8/2010 |
| EP | 2228453 A1 | 9/2010 |
| EP | 2411808 A2 | 2/2012 |
| EP | 2674502 A1 | 12/2013 |
| EP | 2704740 A2 | 3/2014 |
| EP | 2814981 A2 | 12/2014 |
| EP | 2832346 A1 | 2/2015 |
| EP | 3118623 A1 | 1/2017 |
| EP | 3225699 A1 | 10/2017 |
| EP | 3572531 A1 | 11/2019 |
| EP | 3662080 A1 | 6/2020 |
| JP | 2003-344389 A | 12/2003 |
| JP | 4453999 B2 | 4/2010 |
| JP | 2014-012656 A | 1/2014 |
| JP | 2017-058326 A | 3/2017 |
| WO | 90/10715 A1 | 9/1990 |
| WO | 93/05650 A1 | 4/1993 |
| WO | 94/02646 A1 | 2/1994 |
| WO | 95/26417 A1 | 10/1995 |
| WO | 97/45729 A1 | 12/1997 |
| WO | 98/02528 A1 | 1/1998 |
| WO | 98/02740 A1 | 1/1998 |
| WO | 98/44158 A1 | 10/1998 |
| WO | 98/59042 A1 | 12/1998 |
| WO | 99/06594 A1 | 2/1999 |
| WO | 00/00813 A1 | 1/2000 |
| WO | 00/06780 A1 | 2/2000 |
| WO | 00/75647 A1 | 12/2000 |
| WO | 00/77235 A1 | 12/2000 |
| WO | 01/14872 A1 | 3/2001 |
| WO | 01/79851 A1 | 10/2001 |
| WO | 01/98542 A2 | 12/2001 |
| WO | 02/34952 A2 | 5/2002 |
| WO | 02/55985 A2 | 7/2002 |
| WO | 02/56030 A2 | 7/2002 |
| WO | 03/18757 A2 | 3/2003 |
| WO | 03/19141 A2 | 3/2003 |
| WO | 03/35895 A2 | 5/2003 |
| WO | 03/69344 A1 | 8/2003 |
| WO | 03/74730 A1 | 9/2003 |
| WO | 2003/074723 A2 | 9/2003 |
| WO | 03/95974 A2 | 11/2003 |
| WO | 2003/094990 A1 | 11/2003 |
| WO | 2006/100063 A2 | 9/2006 |
| WO | 2007/022483 A2 | 2/2007 |
| WO | 2008/107724 A2 | 9/2008 |
| WO | 2008/111981 A1 | 9/2008 |
| WO | 2009/105499 A1 | 8/2009 |
| WO | 2010/078194 A1 | 7/2010 |
| WO | 2010/096323 A1 | 8/2010 |
| WO | 2010/111388 A2 | 9/2010 |
| WO | 2010/123908 A1 | 10/2010 |
| WO | 2010/132756 A2 | 11/2010 |
| WO | 2011/014741 A1 | 2/2011 |
| WO | 2011/057184 A1 | 5/2011 |
| WO | 2011/082415 A2 | 7/2011 |
| WO | 2012/145662 A1 | 10/2012 |
| WO | 2012/151391 A2 | 11/2012 |
| WO | 2012/166913 A1 | 12/2012 |
| WO | 2013/019290 A2 | 2/2013 |
| WO | 2013/086428 A1 | 6/2013 |
| WO | 2013/123030 A2 | 8/2013 |
| WO | 2013/145870 A1 | 10/2013 |
| WO | 2014/029791 A1 | 2/2014 |
| WO | 2014/049022 A1 | 4/2014 |
| WO | 2015/134053 A1 | 9/2015 |
| WO | 2017/031354 A2 | 2/2017 |
| WO | 2017/201612 A1 | 11/2017 |
| WO | 2017/214310 A1 | 12/2017 |
| WO | 2017/218789 A1 | 12/2017 |
| WO | 2018/022991 A1 | 2/2018 |
| WO | 2018/031903 A1 | 2/2018 |
| WO | 2018/035340 A1 | 2/2018 |
| WO | 2018/145005 A1 | 8/2018 |
| WO | 2019/079743 A1 | 4/2019 |
| WO | 2019/090126 A1 | 5/2019 |
| WO | 2020/140035 A1 | 7/2020 |

OTHER PUBLICATIONS

George et al., RNA Complete BCT™: A novel blood collection tube targeting circulating RNA and extracellular vesicles, Presented at Tricon 2020 (Mar. 3, 2020) and ePoster at AACR 2020 (Apr. 27-28, 2020 & Jun. 22-24, 2020).

Seong et al., Stability of Draw Time microRNA Concentration in RNA Complete BCT™, AACR 2020 (Apr. 27-28, 2020 & Jun. 22-24, 2020).

Liberti et al., Bioreceptor Fenofluids: Novel Characteristics and their Utility in Medical Applications, Supplied by the British Library, Kluwer Academic Publishers; (1996).

Liu et al., Placental mosaicism for Trisomy 13: a challenge in providing the cell-free fetal DNA testing, Journal of assisted reproduction and genetics, 31(5):589-94 (2014).

Lo et al., Commentary: fetal-derived paternally inherited genetic markers in maternal plasma, from molecular testing in laboratory medicine, AACC Press, 264-265 (2002).

Lo et al., Increased Fetal DNA Concentrations in the Plasma of Pregnant Women Carrying Fetuses with Trisomy 21, Clinical Chemistry, 45(10):1747-1751 (1999).

Lo et al., Noninvasive prenatal diagnosis for fetal chromosomal aneuploidies by maternal plasma nucleic acid analysis, Clinical Chemistry, American Association for Clinical Chemistry, 54(3):461-466 (2008).

(56) References Cited

OTHER PUBLICATIONS

Lo et al., Prenatal diagnosis of fetal RhD status by molecular analysis of maternal plasma, N engl. J. med., 1734-1738 (1998).
Lo et al., Prenatal diagnosis: progress through plasma nucleic acids, nature reviews genetics 8:71-77 (2007).
Lo et al., Presence of Fetal DNA in Maternal Plasma and Serum, The Lancet, 350:485-87 (1997).
Lo et al., Quantitative analysis of fetal DNA in maternal plasma and serum: implications for noninvasive prenatal diagnosis, Am. J. Hum. Genet., 62:768-775 (1998).
Lo et al., Quantitative Analysis of Fetal DNA in Maternal Plasma and Serum: Implications for Noninvasive Prenatal Diagnosis, by The American Society of Human Genetics, 62:768-775 (1998).
Lo et al., Rapid clearance of fetal DNA from maternal plasma, Am. J. Hum. Genet., 64:218-224 (1999).
Lo, Circulating Nucleic Acids in Plasma and Serum: An Overview, Annals of the New York Academy of Sciences, 945:1-291 (2001).
Lo, Fetal DNA in maternal plasma/serum: the first 5 years, Pediatr. Res., 53(1):16-17 (2003).
Lo, Fetal DNA in Maternal Plasma: Biology and Diagnostic Applications, Clinical Chemistry, 46(12):1903-1906 (2000).
Lo, Fetal Nucleic Acids in Maternal Plasma, Toward the Development of Noninvasive Prenatal Diagnosis of Fetal Chromosomal Aneuploidies, New York Academy of Sciences, 1137:140-143 (2008).
Lo, Introduction: Plasma DNA and Urinary DNA, pp. 261-263, from Bruns et al. (eds.), Molecular Testing in Laboratory Medicine: Selections from Clinical Chemistry, 1998-2001, AACC Press (2002).
Lo, Molecular Testing of Urine: Catching DNA on the way out, Clinical Chemistry, 46(8):1039-40 (2000).
Locke et al., DNA Methylation Cancer Biomarkers: Translation to the Clinic, Frontiers in Genetics, 10(1150):1-22 (2019).
Loftsson et al., Cyclodextrins in drug delivery, Expert Opin. Drug Deliv., 2:335-351 (2005).
Loftsson et al., Self-association of cyclodextrins and cyclodextrin complexes, J. Pharm. Sci., 93(5):1091-1099 (2004).
Lu et al., Detection and Characterization of Circulating Tumour Cells from Frozen Peripheral Blood Mononuclear Cells, Journal of Circulating Biomarkers, 35(12):1243-6 (2015).
Lui et al., Circulating DNA in plasma and serum: Biology, Preanalytical issues and diagnostic applications, Clin. Chem. Lab. Med., 40(10):962-968 (2002).
Lui et al., Predominant hematopoietic origin of cell-free DNA in plasma and serum after sex-mismatched bone marrow transplantation, Clinical Chemistry, 48(3):421-427 (2002).
Luk et al., CTC-mRNA (AR-V7) Analysis from Blood Samples— Impact of Blood Collection Tube and Storage Time, Int. J. Mol. Sci., 18(5):1047 (2017).
Lutz et al., Release of spectrin-free vesicles from human erythrocytes during ATP depletion. I. Characterization of spectrin-free vesicles, J. Cell Biol., 73(3):548-60 (1977).
Machaca et al., Characterization of apoptosis-like endonuclease activity in avian thymocytes, Biology of the Cell, 76(1):15-22 (1992).
Madabusi et al., RNA extraction for arrays, Methods in Enzymology, 411:1-14 (2006).
Magnette et al., Pre-analytical issues in the haemostasis laboratory: guidance for the clinical laboratories, Thromb J., 14:49 (2016).
Mahammad et al., Cholesterol depletion using methyl-beta-cyclodextrin, Methods in Membrane Lipids, 91-102 (2015).
Makhro et al., Red cell properties after different modes of blood transportation, Front Physiol., 7:288 (2016).
Markus et al., Evaluation of pre-analytical factors affecting plasma DNA analysis, Sci. Rep., 8(1):7375 (2017).
Marrinucci et al., Cytomorphology of circulating colorectal tumor cells:a small case series, J. Oncol., 2010:861341 (2010).
Maunier et al., Can stabilization of whole blood samples with Cytochex (Trademark) allow test batching of CD55 and CD59 deficiency flow cytometry analysis?, Cellquant-redquant CD55/CD59, 1-8 (2012).
May et al., How Many Species Are There On Earth?, Science, 241:1441-1449 (1988).
McCoy, Ch. 10: Preparation of cells from blood, Methods in Cell Biology, 63 (2001).
McCullough et al., Non-invasive prenatal chromosomal aneuploidy testing-clinical experience: 100,000 clinical samples, PLoS One, 9(10):e109173 (2014).
Mellert et al., Development and clinical utility of a blood-based test service for the rapid identification of actionable mutations in non-small cell lung carcinoma, J. Mol. Diag., 19(3):404-416 (2017).
Merriam-Webster'S Medical Dictionary, p. 606, Springfield, MA: Merriam-Webster Incorporated (1995).
Milde et al., Improved DNA typing of human urine by adding EDTA, Int. J. Legal Med., 112(3):209-210 (1999).
Miller et al., A Simple Salting Out Procedure for Extracting DNA from Human Nucleated Cells, Nucleic Acids Research, 16(3):1215 (1988).
Miller-Lindholm et al., Streck cell preservative preserves bone marrow specimens, Streck Cell Preservative Application Note Issue 1, 320024-2, 1-4 (2004).
Minear et al., Global perspectives on clinical adoption of NIPT, Prenat. Diagn., 35(10):959-967 (2015).
Modrek et al., Genome-wide Detection of Alternative Splicing in Expressed Sequences of Human Genes, Nucleic Acid Research, 29(13):2850-2859 (2001).
Motoyama et al., Effect of 2,6-di-O-methyl-alpha-cyclodextrin on hemolysis and morphological change in rabbit's red blood cells, Eur. J. Pharm. Sci., 29(2):111-9 (2006).
Motoyama et al., Involvement of lipid rafts of rabbit red blood cells in morphological changes induced by methylated beta-cyclodextrins, Biol. Pharm. Bull., 32(4):700-5 (2009).
Murray et al., "Future-Proofing" Blood Processing for Measurement of Circulating miRNAs in Samples from Biobanks and Prospective Clinical Trials, Cancer Epidemiol Biomarkers Prev., 27(2):208-218 (2018).
Murugesan et al., Investigation of Preanalytical Variables Impacting Pathogen Cell-Free DNA in Blood and Urine, Journal of Clinical Microbiology, 57(11):1-13 (2019).
Nace et al., Evaluation of Streck tissue fixative, a nonformalin fixative for preservation of stool samples and subsequent parasitologic examination, J. Clin. Microbiology, 37(12):4113-4119 (1999).
Nair et al., An observational study of circulating tumor cells and (18) F-FDG PET uptake in patients with treatment-naive non-small cell lung cancer, PloS One, 8(7):e67733 (2013).
Nicholson et al., Inactivation of HIV-infected H9 cells in whole blood preparations by lysing/fixing reagents used in flow cytometry, J. Immunol. Methods, 160:215-218 (1993).
Chan et al., Hypermethylated RASSFIA in maternal Plasma: A Universal Fetal DNA Marker that Improves the Reliability of Noninvasive Prenatal Diagnosis, Clinical Chemistry, 52(12):2211-2218 (2006).
Chan et al., Size distributions of maternal and fetal DNA in maternal plasma, clinical chemistry, 50(1):88-92 (2004).
Chang et al., Review of the clinical applications and technological advances of circulating tumor DNA in cancer monitoring, The Clin. Risk Manag., 13:1363-1374 (2017).
Cherepanova et al., Immunochemical assay for deoxyribonuclease activity in body fluids, Journal of immunological methods, 325(1):96-103 (2007).
Chinnapapagari et al., Treatment of maternal blood samples with formaldehyde does not alter the proportion of circulatory fetal nucleic acids (DNA and mRNA) in maternal plasma, Clin Chem., 51(3):652-5 (2005).
Chiu et al., Effects of blood-processing protocols on fetal and total DNA quantification in maternal plasma, Clin. Chem., 47(9):1607-1613 (2001).
Chiu et al., Effects of Blood-Processing Protocols on Fetal and Total DNA Quantification in Maternal Plasma, Clinical Chemistry, 47(9):1607-1613 (2001).
Chu et al., ESR1 mutations in circulating plasma tumor DNA from metastatic breast cancer patients, Clin. Cancer Res., 22(4):993-999 (2016).

(56) References Cited

OTHER PUBLICATIONS

Chudziak et al., Clinical evaluation of a novel microfluidic device for epitope-independent enrichment of circulating tumour cells in patients with small cell lung cancer, The Analyst, 141(2):669-78 (2015).
Chung et al., Detrimental Effect of Formaldehyde on Plasma RNA Detection, Clin. Chem., 51(6):1074-6 (2005).
Chung et al., Lack of Dramatic Enrichment of Fetal DNA in Maternal Plasma by Formaldehyde Treatment, Clinical Chemistry, 51(3):655-8 (2005).
Chutkan et al., Quantitative and qualitative preparations of bacterial outer membrane vesicles, Methods Mol. Biol., 966:259-272 (2013).
Clark-Ganheart et al., Use of Cell-Free DNA in the Investigation of Intrauterine Fetal Demise and Miscarriage, Obstetrics & Gynecology, 125(6):1321-9 (2015).
Clausen et al., Noninvasive fetal RhD genotyping, Transfusion and Apheresis Science, (2014).
Clayton et al., Considerations towards a roadmap for collection, handling and storage of blood extracellular vesicles, J. Extracell. Vesicles, 8(1):1647027 (2019).
Clinical Applications of Flow Cytometry: Immunophenotyping of Leukemic Cells; Approved Guideline; NCCLS, 18(8) (1998).
Colombo et al., Biogenesis, secretion, and intercellular interactions of exosomes and other extracellular vesicles, Annu. Rev. Cell Dev. Biol., 30:255-89 (2014).
Comas et al., Initial Experience with Non-Invasive Prenatal Testing of Cell-Free DNA for Major Chromosomal Anomalies in a Clinical Setting, The Journal of Maternal-Fetal & Neonatal Medicine, 28(10): 1-6 (2014).
Connelly et al., "Antibiotic Resistance Monitoring and Detection (ARM-D(TM)) PCR Kits: ARM-D(TM) for [beta]-Lactamase ID—Technical Note", Bio. Tech. Rap. Disp., 57(6):317-318 (2014).
Costa et al., Fetal Expressed Gene Analysis in maternal Blood: A New Tool for Noninvasive Study of the Fetus, Clinical Chemistry, 49(6):981-983 (2003).
Curnow et al., Detection of Triploid, Molar, and Vanishing Twin Pregnancies by a Single-Nucleotide Polymorphism-Based Noninvasive Prenatal Test, American Journal of Obstetrics and Gynecology, 212(1):79.e1-9 (2015).
Das et al., Effects of a novel cell stabilizing reagent on DNA amplification by PCR as compared to traditional stabilizing reagents, Acta Histochemica., 116:55-60 (2014).
Das et al.,, Effects of a novel cell stabilizing reagent on DNA amplification by PCR as compared to traditional stabilizing reagents, Acta Histochemica; 116(1):55-60 (2014).
Dash et al., Using Noninvasive Prenatal Testing for Aneuploidies in a Developing Country: Lessons Learnt, Journal of Fetal Medicine, 1(3):131-5 (2014).
Davis et al., Stability of immunophenotypic markers in fixed peripheral blood for extended analysis using flow cytometry, J. Immunol. Methods, 363:158-165 (2011).
De Miranda et al., Cyclodextrins and ternary complexes: technology to improve solubility of poorly soluble drugs, Br. J. Pharm. Sci., 47(4):665-81 (2011).
Dean et al., Comprehensive human genome amplification using multiple displacement amplification, Pro. Nat. Acad. Sci., 99(8):5261-5266 (2002).
Deatherage et al., Membrane Vesicle Release in Bacteria, Eukaryotes, and Archaea: a Conserved yet Underappreciated Aspect of Microbial Life, Infection and Immunity, 80(6):1948-1957 (2012).
Denis et al., Efficient Detection of BRAF Mutation in Plasma of Patients after Long-term Storage of Blood in Cell-Free DNA Blood Collection Tubes, Clinical Chemistry, 61(6):886-8 (2015).
Dessel et al., Application of circulating tumor DNA in prospective clinical oncology trials—standardization of preanalytical conditions, Mol. Oncol., 11(3):295-304 (2017).
Dhallan et al., A noninvasive test for prenatal diagnosis based on fetal DNA present in maternal blood: a preliminary study, The Lancet.; 369 (9560):474-481 (2007).
Dhallan et al., Methods to Increase the Percentage of Free Fetal DNA Recovered from the Maternal Circulation, JAMA, 291(9):1114-1119 (2004).
Dharajiya et al., Noninvasive Prenatal Testing Using Cell-Free Fetal DNA in Maternal Plasma, Current Protocols in Human Genetics, 84:8-15 (2015).
Diamond et al., Diverse and Targetable Kinase Alterations Drive Histiocytic Neoplasms, Cancer discovery, 6(2):154-65 (2016).
Diaz et al., Performance of streck cfDNA blood collection tubes for liquid biopsy testing, PLoS One, 11(11):e0166354 (2016).
Ding, et al., MS Analysis of Single-Nucleotide, Differences in Circulating Nucleic Acids: Application to Noninvasive Prenatal Diagnosis, Proc. Natl. Acad. Sci. USA, 101:10762-10767 (2004).
Dumaswala et al., Improved red blood cell preservation correlates with decreased loss of bands 3, 4.1, acetylcholinestrase, and lipids in microvesicles, Blood, 87(4):1612-6 (1996).
EP Application No. 10000518.0 (Patent No. EP2228453), Brief communication regarding Letter from the opponent 02 (Cenata) of Jun. 6, 2018 including exhibits, dated Jun. 14, 2018.
EP Application No. 10000518.0 (Patent No. EP2228453), Brief communication to Opponent 1 and Opponent 2 dated May 29, 2018 and Reply including exhibits of patent proprietor to notice(s) of opposition dated Apr. 26, 2018.
European application No. 03 256 535.0-2113, Decision to refuse a European Patent application, Mailed May 30, 2007.
European Application No. 10000518.0, Communication of a notice of intervention including exhibits by Cenata GmbH, mailed Apr. 13, 2018.
European Application No. 10000518.0, Communication of a notice of opposition including exhibits, mailed Sep. 12, 2017.
European Application No. 10704474.5, European Patent Office Summons to Attend, mailed Jan. 27, 2016.
European Application No. 10704474.5, European Third Party Observations, mailed Aug. 30, 2016.
European Application No. 13706856.5, European Communication of a notice of opposition including exhibits, mailed Mar. 28, 2018.
European Application No. 13706856.5, European Third Party Observations, mailed May 25, 2016.
European Application No. 16199783, European Search Report and Opinion, mailed Feb. 17, 2017.
European Application No. 18867969, European Search Report and Opinion, mailed Jun. 30, 2021.
European Application No. 19186944, European Search Report and Opinion, mailed Oct. 17, 2019.
European Application No. EP 17 84 2131, Supplementary partial search report, mailed Mar. 16, 2020.
Fairbrother et al., Clinical experience of noninvasive prenatal testing with cell-free DNA for fetal trisomies 21, 18, and 13, in a general screening population, Prenatal Diagnosis, 33(6):580-3 (2013).
Fan et al., Analysis of the size distributions of fetal and maternal cell-free DNA by paired-end seauencing, clinical chemistry, 56(8):1279-1286 (2010).
Fan et al., Noninvasive diagnosis of fetal aneuploidy by shotgun sequencing DNA from maternal blood, PNAS., 105(42):16266-16271 (2008).
Fernando et al., A new methodology to preserve the original proportion and integrity of cell-free fetal DNA in maternal plasma during sample processing and storage, 30(5):418-424 (2010).
Fernando et al., Stabilization of cell-free RNA in blood samples using a new collection device, Clinical Biochemistry, 45(16-17):1497-1502 (2012).
Fernando et al., Stabilization of cell-free RNA in plasma for noninvasive diagnosis and prognosis, retrieved from the internet: URL: http://www.streck.com/resources/cell_stabilization/cell-free_RNA_BCT_Stabilization_of_Cell-Free_RNA_in_Plasma.pdf (2010).
Fiebelkorn et al., Clinical evaluation of an automated nucleic acid isolation system, Clin. Chem., 48(9):1613-1615 (2002).
Finning et al., The use of maternal plasma for prenatal RhD blood group genotyping, Methods Mol. Biol., 496:143-57 (2009).
Fleischhacker et al., Methods for isolation of cell-free plasma DNA strongly affect DNA yield, Clinica. Chimica. Acta, 412:2085-2088 (2011).

(56) References Cited

OTHER PUBLICATIONS

Fomovsky et al., Centrifuge-free isolation of liquid plasma from clinical samples from whole blood (2012).

Foy et al., Emerging homogeneous technologies for bioanalysis, Clin. Chem., 47(6)990-100 (2001).

Francis et al., Rapid single step method for flow cytometric detection of surface and intracellular antigens using whole blood, Cytometry, 25:58-70 (1996).

Funasaki et al., Mechanisms and surface chemical prediction of imipramine-induced hemolysis suppressed by modified cyclodextrins, J. Pharm. Sci., 90(8):1056-65 (2001).

Futch et al., Initial clinical laboratory experience in noninvasive prenatal testing for fetal aneuploidy from maternal plasma DNA samples, Prenatal Diagnosis, 33(6):569-74 (2013).

Gahlawat et al., Evaluation of storage tubes for combined analysis of circulating nucleic acids in liquid biopsies, Int. J. Mol. Sci., 20(3):704 (2019).

George et al., Cell-free RNA next-generation sequencing workflow for the Streck RNA Complete BCT, Streck (Jan. 2021).

George et al., RNA Complete BCT (RNAC) maintains draw-time concentrations of extracellular vesicles (EVs) and associated cell-free RNA (cfRNA), streck, (Feb. 2021).

George et al., RNA Complete BCT(Trademark): A novel blood collection tube targeting circulating RNA and extracellular vesicles, streck, ePoster 759, AACR, (2020).

Gheinani et al., Improved isolation strategies to increase the yield and purity of human urinary exosomes for biomarker discovery, Scientific Reports, 8:3945 (2018).

Gielis et al., Cell-Free DNA: An Upcoming Biomarker in Transplantation, Am. J. Transplant., 15(10):2541-51 (2015).

Gil et al., Cell-free DNA analysis for trisomy risk assessment in first-trimester twin pregnancies, Fetal Diagnosis and Therapy, 35(3):204-11 (2013).

Gil et al., Implementation of maternal blood cell-free DNA testing in early screening for aneuploidies, Ultrasound in Obstetrics & Gynecology, 42(1):34-40 (2013).

Gil et al., UK NHS pilot study on cell-free DNA testing in screening for fetal trisomies: factors affecting uptake, Ultrasound in Obstetrics & Gynecology, 45(1):67-73 (2015).

Gogoi et al., Development of an automated and sensitive microfluidic device for capturing and characterizing circulating tumor cells (CTCs) from clinical blood samples, PLoS One, 11(1):e0147400 (2016).

Gonzales et al., Application of Fetal DNA Detection in Maternal Plasma: A Prenatal Diagnosis Unit Experience, Journal of Histochemistry & Cytochemistry, 53(3):307-314 (2005).

Greene et al., Chromosomal instability estimation based on next generation sequencing and single cell genome wide copy number variation analysis, PLoS One, 11(11):e0165089 (2016).

Greenwalt et al., Erythrocyte membrane vesiculation and changes in membrane composition during storage in citrate-phosphate-dextrose-adenine-1, Vox Sang., 47(4):261-70 (1984).

Greer et al., PCR amplification from paraffin-embedded tissues, Am. J. Clin. Pathol., 95(2):117-124 (1991).

Grölz et al., Liquid biopsy preservation solutions for standardized pre-analytical workflows-venous whole blood and plasma, Curr. Pathobiol. Rep., 6(4):275-286 (2018).

Gromminger et al., Fetal aneuploidy detection by cell-free DNA sequencing for multiple pregnancies and quality issues with vanishing twins, Journal of Clinical Medicine, 3(3):679-92 (2014).

Gross et al., Rapid changes in circulating tumor cells following anti-angiogenic therapy, Convergent Science Physical Oncology, 1(1):015002 (2015).

Grskovic et al., Validation of a clinical-grade assay to measure donor-derived cell-free DNA in solid organ transplant recipients, J. Mol. Diagn., 18(6):890-902 (2016).

Guo et al., RNAseq by Total RNA Library Identifies Additional RNAs Compared to Poly(A) RNA Library, Biomed. Res. Int., 2015:862130 (2015).

György et al., Improved circulating microparticle analysis in acid-citrate dextrose (ACD) anticoagulant tube, Thromb. Res., 133(2):285-92 (2014).

Haaland, Molecules and models: the molecular structures of main group element compounds Oxford University Press, (abstract available at http://www.oxfordscholarship.com/view/10.1093/acprof:oso/9780199235353.001.0001/acprof-9780199235353-chapter-12) (2018).

Hallick et al., Use of Aurintricarboxylic Acid as in Inhibitor of Nucleases During Nucleic Acid Isolation, Nucleic Acid Research, 4:3055-3064 (1977).

Hanessian et al., The Synthesis of functionalized cyclodextrins as scaffolds and templates for molecular diversity, Catalysis, and Inclusion Phenomena, J. Org. Chem., 60(15):4786-4797 (1995).

Harmony prenatal test—IVD Kit—P/N 08011281001 (FGK1002)—Instructions for use, Retrieved from the internet on or around, 31 (2018).

Herrera et al., Cell-free DNA, inflammation, and the initiation of spontaneous term labor, Am. J. Obstet. Gynecol., 217(5):583.e1-583.e8 (2017).

Hidestrand et al., Influence of temperature during transportation on cell-free DNA analysis, Fetal diagnosis and Therapy, 31(2):122-8 (2012).

Hindson et al., High-throughput droplet digital PCR system for absolute quantitation of DNA copy number, Analytical Chemistry, 83(22):8604-10 (2011).

Holford et al., Stability of beta-actin mRNA in plasma, Annals of the New York Academy of Science, 1137:108-111 (2008).

Holmberg et al., Akonni TruTip(®) and Qiagen(®) methods for extraction of fetal circulating DNA-evaluation by real-time and digital PCR, PloS One, 8(8):e73068 (2013).

Holodniy et al., Determination of human immunodeficiency virus RNA in plasma and cellular viral DNA genotypic zidovudine resistance and viral load during zidovudine-didanosine combination therapy, J. Virology, 69(6):3510-3516 (1995).

Hooks et al., Non-invasive risk assessment of fetal sex chromosome aneuploidy through directed analysis and incorporation of fetal fraction, Prenatal Diagnosis, 34(5):496-9 (2014).

Hrebien et al., Reproducibility of digital PCR assays for circulating tumor DNA analysis in advanced breast cancer, PLoS One, 11(10):e0165023 (2016).

Hulten et al., Non-invasive prenatal diagnosis: an epigenetic approach to the detection of common fetal chromosome disorders by analysis of maternal blood samples, Circulating Nucleic Acids In Plasma and Serum, 133-142 (2011).

Hyland et al., Non-invasive fetal RHD genotyping for RhD negative women stratified into RHD gene deletion or variant groups: comparative accuracy using two blood collection tube types, Pathology, 49(7):757-764 (2017).

Hynek et al., MoM-based Approach to Noninvasive Prenatal Testing Using Exponentially Weighted. Moving Average Chart and Chromosomal Fingerprint, International Journal of Biomedicine and Healthcare, 3(2):12-15 (2015).

Ignatiadis et al., Circulating Tumor Cells and Circulating Tumor DNA: Challenges and Opportunities on the Path to Clinical Utility, Clinical. Cancer Research, 21(21):4786-800 (2015).

Zill et al., Cell-free DNA next-generation sequencing in pancreatobiliary carcinomas, Cancer discovery, 5(10):1040-8 (2015).

Alidousty et al., Comparison of blood collection tubes from three different manufacturers for the collection of cell-free DNA for liquid biopsy mutation testing, J. Mol. Diagnostics, 19(5):801-804 (2017).

Almizraq et al., Characteristics of Extracellular Vesicles in Red Blood Concentrates Change with Storage Time and Blood Manufacturing Method, Transfus. Med. Hemother., 45(3):185-193 (2018).

Alvarez et al., Comparison of protein, microRNA, and mRNA yields using different methods of urinary exosome isolation for the discovery of kidney disease biomarkers, Kidney International 82:1024-1032 (2012).

Ames et al., An Appraisal of the "Vacutainer" System for Blood Collection, Ann. Clin. Biochem., 12:151-155 (1975).

Amicucci et al., Prenatal diagnosis of myotonic dystrophy using fetal DNA obtained from maternal plasma, Clin. Chem., 46(2):301-302 (2000).

(56) References Cited

OTHER PUBLICATIONS

Amitani et al., Allantoin ameliorates chemically-induced pancreatic (Beta)-cell damage through activation of the imidazoline 13 receptors, PeerJ. 3:e1105 (2015).
Ammerlaan et al., Method validation for preparing serum and plasma samples from human blood for downstream proteomic, metabolomic, and circulating nucleic acid-based applications, Biopreserv Biobank.; 12(4):269-80 (2014).
Angert et al., Fetal Cell-free Plasma DNA Concentrations in Maternal Blood Are Stable 24 Hours after Collection: Analysis of First- and Third-Trimester Samples, Clinical-Chemistry, 49(1):195-198 (2003).
Anitua, Plasma rich in growth factors: preliminary results of use in the preparation of future sites for implants, Int J Oral Maxillofac Implants; 14(4):529-35 (1999).
Anker et al., Circulating nucleic acids In plasma and serum as a noninvasive investigation for cancer: Time for large-scale clinical studies?, Int. J. Cancer, 103:149-152 (2003).
Arikan, A comparison of the effect of methyl-beta-cyclodextrin on the osmotic fragility of ovine, bovine and human erythrocytes, Turk J. Vet. Anim. Sci., 27:383-387 (2003).
Arroyo et al., Argonaute2 complexes carry a population of circulating microRNAs independent of vesicles in human plasma, Proc. Natl. Acad. Sci., 108(12):5003-5008 (2011).
Ashoor et al., Fetal fraction in maternal plasma cell-free DNA at 11-13 weeks' gestation: relation to maternal and fetal characteristics, ultrasound obstet gynecol., 41:26-32 (2013).
Ashoor et al., Trisomy 13 detection in the first trimester of pregnancy using a chromosome-selective cell-free DNA analysis method, Ultrasound in Obstetrics & Gynecology, 41(1):21-5 (2012).
Augustus et al., The art of obtaining a high yield of cell-free DNA from urine, PLoS ONE, 15(4):e0231058:1-22 (2020).
Banfi et al., The role of ethylenediamine tetraacetic acid (EDTA) as in vitro anticoagulant for diagnostic purposes, Clin. Chem. Lab. Med., 45(5):565-576 (2007).
Barra et al., EDTA-mediated inhibition of DNases protects circulating cell-free DNA from ex vivo degradation in blood samples, clinical biochemistry, 48:976-81 (2015).
Barrett et al., Implementing Prenatal Diagnosis Based on Cell-Free Fetal DNA. Accurate Identification of Factors Affecting Fetal DNA Yield, PLoS One, 6(10):e25202 (2011).
Bayindir et al., Noninvasive Prenatal Testing Using a Novel Analysis Pipeline to Screen for All Autosomal Fetal Aneuploidies Improves Pregnancy Management, European Journal of Human Genetics, 23(10):1286-93 (2015).
Beck et al., Digital Droplet PCR for Rapid Quantification of Donor DNA in the Circulation of Transplant Recipients as a Potential Universal Biomarker of Graft Injury, Clinical chemistry, 59(12):1732-41 (2013).
Benachi et al., Cell-Free DNA Analysis in Maternal Plasma in Cases of Fetal Abnormalities Detected on Ultrasound Examination, Obstetrics & Gynecology, 125(6):1330-7 (2015).
Benachi et al., Impact of formaldehyde on the in vitro proportion of fetal DNA in maternal plasma and serum, Clin. Chem., 51(1):242-244 (2005).
Bergholtz et al., Confirmation of equivalence of one-spin and two-spin protocols for plasma isolation from Lbgard(Registered) blood tubes, biomatrica., (2018).
Bethel et al., Fluid phase biopsy for detection and characterization of circulating endothelial cells in myocardial infarction, Physical biology, 11(1):016002 (2014).
Bevilacqua et al., Performance of screening for aneuploidies by cell-free DNA analysis of maternal blood in twin pregnancies, Ultrasound in Obstetrics & Gynecology, 45(1):61-6 (2015).
Bianchi et al., DNA sequencing versus standard prenatal aneuploidy screening, New England Journal of Medicine, 370(9):799-808 (2014).
Bianchi et al., Fetal sex chromosome testing by maternal plasma DNA sequencing: clinical laboratory experience and biology, Obstetrics & Gynecology, 125(2):375-82 (2015).
Bianchi et al., PCR Quantifications of Fetal Cells in Maternal Blood in Normal and Aneuploid Pregnancies, Am. J. Hum. Genet., 61:822-29 (1997).
Bianchi, Invited Editorial Fetal DNA in Maternal Plasma: The Plot Thickens and the Placental Barrier Thins, by The American Society of Human Genetics, 62:763-764 (1998).
Bina-Stein et al., Aurintricarboxylic Acid Is a Nonspecific Enzyme Inhibitor, Department of Chemistry, Yak University, New Haven, Connecticut, 12:191-193 (1975).
Biocept (BIOC) Announces Patent for Blood Collection and Transport Tube; StreetInsider.com; http://www.streetinsider.com/corporate+news/biocept+(BIOC)+Announces; (2015).
Biocept—Expands Patent Protection for Liquid Biopsy Platform; http://ir.biocept.com/releasedetail.cfm?releaseID=915635 (2015).
Biocept Completing the Answer; http://ir.biocept.com/secfiling.cfm?filingid=1193125-15-16425%cik=1044378. (2015).
Bloom et al., Cell-free DNA and active rejection in kidney allografts, J. Am. Soc. Nephrol., 28(7):2221-2232 (2017).
Boddy et al., Prospective study of quantitation of plasma DNA levels in the diagnosis of malignant versus benign prostate disease. Clinical cancer research, 11(4):1394-1399 (2005).
Boffa et al., Cellular expression of PD-L1 in the peripheral blood of lung cancer patients is associated with worse survival, Cancer Epidemiol. Biomarkers Prev., 26(7):1139-1145 (2017).
Botezatu et al., Genetic Analysis of DNA Excreted in Urine: A New Approach for Detecting Specific Genomic DNA Sequences from Cells Dying in an Organism, Clinical Chemistry, 46(8):1078-1084 (2000).
Brar et al., The fetal fraction of cell-free DNA in maternal plasma is not affected by a priori risk of fetal trisomy, The Journal of Maternal-Fetal & Neonatal Medicine, 26(2):143-5 (2013).
Brown et al., A novel flow cytometry stimulation assay using cyto-ches(Registered) BCT tubes for use in clinical trials, Flow contract site laboratory, 1 (2011).
Brown, Effect of Blood Collection and Processing on Radioimmunoassay Results for Apolipoprotein B in Plasma, Clinical Chemistry, 36(9):1662-1666 (1990).
Bruno et al., Use of copy number deletion polymorphisms to assess DNA chimerism, Clinical chemistry, 60(8):1105-14 (2014).
Butler, Genetics and Genomics of Core Short Tandem Repeat Loci Using in Human Identity Testing, Journal of Forensic Science, 51(2):253-265 (2006).
Buysse et al., Reliable noninvasive prenatal testing by massively parallel sequencing of circulating cell-free DNA from maternal plasma processed up to 24h after venipuncture, Clinical biochemistry, 46(18):1783-6 (2013).
Byron et al., Translating RNA sequencing into clinical diagnostics: opportunities and challenges, Nat. Rev. Genet., 17(5):257-71 (2016).
Campbell et al., Analytical and biological considerations in the measurement of cell-associated CCR5 and CXCR4 mRNA and protein, Clin. Vaccine Immun., 17(7):1148-1154 (2010).
Camunas-Soler et al., Noninvasive prenatal diagnosis of single-gene disorders by use of droplet digital PCR, Clin. Chem., 64(2):336-345 (2017).
Cannas et al., Implications of storing urinary DNA from different populations for molecular analyses, PloS one, 4(9):e6985 (2009).
Carlsson et al., Circulating Tumor Microemboli Diagnostics for Patients with Non-Small-Cell Lung Cancer, Journal of Thoracic Oncology, 9(8):1111-9 (2014).
Catellier et al., Atherosclerosis risk in communities (ARIC) carotid MRI flow cytometry study of monocyte and platelet markers: intraindividual variability and reliability, Clinical Chemistry 54(8):1363-1371 (2008).
Cell-free DNA collection tube roche (2016).
Salvianti et al., The pre-analytical phase of the liquid biopsy, N. Biotechnol., 55:19-29 (2020).
Samango-Sprouse et al., SNP-based non-invasive prenatal testing detects sex chromosome aneuploidies with high accuracy, Prenatal diagnosis, 33(7):643-9 (2013).
Samoila et al., Method development and validation for clinical cfDNA extraction from blood, InASCO Annual Meeting Proceedings, 33(15_suppl):e22185 (2015).

(56) References Cited

OTHER PUBLICATIONS

Samuel et al., The effect of chorionic villus sampling on the fraction of cell-free fetal DNA in maternal plasma, The Journal of Maternal-Fetal &. Neonatal Medicine, 15:1-4 (2015).
Saxton et al., Effect of ex vivo storage on human peripheral blood neutrophil expression of CD11b and the stabilizing effects of Cyto-Chex, J. Immunol. Methods, 214:11-17 (1998).
Schatz et al., Preservation of Cell-Free DNA in Stored Blood Samples for the Analysis of the (M) Sept9 Colorectal Cancer Screening Marker Enables Sample Shipment by Mail, Published as a poser at the conference on International federation of clinical chemistry and laboratory medicine Worldlab and EU, Berlin, Germany (2011).
Scheffer et al., Noninvasive fetal blood group genotyping of rhesus D, c, E and of K in alloimmunised pregnant women: evaluation of a 7-year clinical experience, BJOG: An International Journal of Obstetrics & Gynaecology, 118(11):1340-8 (2011).
Scher et al., Association of AR-V7 on circulating tumor cells as a treatment-specific biomarker with outcomes and survival in castration-resistant prostate cancer, JAMA. Oncol., 2(11):1441-1449 (2016).
Schiavon et al., Analysis of ESR1 mutation in circulating tumor DNA demonstrates evolution during therapy for metastatic breast cancer, Science translational medicine, 7(313):313ra182 (2015).
Sekizawa et al., Apoptosis in Fetal Nucleated Erythrocytes Circulating in Maternal Blood, Prenatal Diagnosis, 20:886-889 (2000).
Seo et al., An Experience of Using the Harmony Test for Genomics-Based Non-Invasive Prenatal Testing, Journal of Laboratory Medicine and Quality Assurance, 37(1):44-6 (2015).
Seong et al., Stability of Draw Time microRNA Concentration in RNA Complete BCT, streck, ePoster 4831, AACR (2020).
Sherwood et al., Optimised pre-analytical methods improve KRAS mutation detection in circulating tumour DNA (ctDNA) from patients with non-small cell lung cancer (NSCLC), PLoS One, 11(2):e0150197 (2016).
Shi et al., Feasibility of noninvasive prenatal testing for common fetal aneuploidies in an early gestational window, Clinica. Chimica. Acta., 439:24-8 (2015).
Sigma-Aldrich, 1-Aza-3,7-dioxabieyclo[3.3.0]octane-5-methanol solution, Available online at <www.sigmaaldrich.com/catalog/product/aldrich/417807?lang=en%region=US>, 5 pages, Accessed Jan. 13, 2014.
Sillence et al., Fetal Sex and RHD Genotyping with Digital PCR Demonstrates Greater Sensitivity than Real-time PCR, Clinical Chemistry, 61(11):1399-407 (2015).
Skidmore et al., Characterization and Use of the Potent Ribonuclease Inhibitor Aurintricarboxylic Acid for the Isolation of RNA from Animal Tissues, Biochem Journal, 263(1):73-80 (1989).
Slocum et al., Electron-Microscopic Cytochemical Localization of Diamine and polyamine oxidases in Pea and Maize Tissues, Planta., 183:443-450 (1991).
Smid et al., Evaluation of Different Approaches for Fetal DNA Analysis from Maternal Plasma and Nucleated Blood Cells, Technical Briefs, 45(9):1570-1572 (1999).
Smid et al., Quantitative Analysis of Fetal DNA in Maternal Plasma in Pathological Conditions Associated with Placental Abnormalities, Annals New York Academy of Sciences, 951:133-137 (2001).
Smit et al., Semiautomated DNA Mutation Analysis Using a Robotic Workstation and Molecular Beacons, Clinical Chemistry, 47:739-744 (2001).
Smith et al., Targeted mutation detection in breast cancer using MammaSeq (Trademark), Breast Cancer Research, 21(1):22 (2019).
Song et al., Non-invasive prenatal testing for fetal aneuploidies in the first trimester of pregnancy, Ultrasound in Obstetrics & Gynecology, 45(1):55-60 (2015).
Sparks et al., Noninvasive prenatal detection and selective analysis of cell-free DNA obtained from maternal blood: evaluation for trisomy 21 and trisomy 18, Americana Journal of Obstetrics and Gynecology, 206(4):319-e1-9 (2012).
Sparks et al., Selective analysis of cell-free DNA in maternal blood for evaluation of fetal trisomy, prenatal diagnosis 32:3-9 (2012).
Springer et al., Evaluation of a new reagent for preserving fresh blood samples and its potential usefulness for internal quality controls of multichannel hematology analyzers, Am. J. Clin. Pathol., 111:387-396 (1999).
Stokowski et al., Clinical performance of non-invasive prenatal testing (NIPT) using targeted cell-free DNA analysis in maternal plasma with microarrays or next generation sequencing (NGS) is consistent across multiple controlled clinical studies, Prenatal Diagnosis, 35(12):1243-6 (2015).
Stokowski et al., Evaluation of automated cell-free DNA extraction methods with the harmony(Registered) prenatal test, roche seauencina solutions, roche diagnostics, Inc. (2018).
Streck et al., 1-XP55419765A, Product Summary: Cell-Free DNA(Trademark) BCT, (2009).
Strom et al., Improving the positive predictive value of non-invasive prenatal screening (NIPS), PLOS one, 12(3):e0167130 (2017).
Stumm et al., Diagnostic accuracy of random massively parallel sequencing for non-invasive prenatal detection of common autosomal aneuploidies: a collaborative study in Europe, Prenatal Diagnosis, 34(2):185-91 (2014).
Su et al., Detection of a K-ras mutation in urine of patients with colorectal cancer, Cancer Biomarkers, 1(2-3):177-82 (2005).
Suwinski et al., Advancing Personalized Medicine Through the Application of Whole Exome Sequencing and Big Data Analytics, Front. Genet., 10:49 (2019).
Swarup et al., Circulating (cell-free) Nucleic Acids—A Promising, Non-Invasive Tool for Early Detection of Several Human Diseases, FEBS Letters, 481:795-799 (2007).
Szarvas et al., Determination of Endogenous Formaldehyde Level in Human Blood and Urine by Dimedone-14C Radiometric Method, J. Radioanal. Nucl. Chem., Letters; 106, 357-367 (1986).
Takabayashi et al., Development of Non-invasive Fetal DNA Diagnosis from Maternal Blood, Prenatal Diagnosis, 15:74-77 (1995).
Taylor-Phillips et al., Accuracy of non-invasive prenatal testing using cell-free DNA for detection of down, Edwards and patau syndromes: a systematic review and meta-analysis, BMJ. Open., 6(1):e010002 (2016).
Thompson et al., Detection of therapeutically targetable driver and resistance mutations in lung cancer patients by next-generation sequencing of cell-free circulating tumor DNA, Clin. Cancer Res., 22(23):5772-5782 (2016).
Thung et al., Implementation of whole genome massively parallel sequencing for noninvasive prenatal testing in laboratories, Expert Review of Molecular Diagnostics, 15(1):111-24 (2015).
Tong et al., Diagnostic developments involving cell-free (circulating) nucleic acids, Clinica. Chimica. Acta., 363(1):187-96 (2006).
Toro et al., Comparison of cell stabilizing blood collection tubes for circulating plasma tumor DNA, Clinical Biochemistry, 48(15):993-8 (2015).
Toro, Detection of PIK3CA Mutations in Plasma Tumor DNA Circulating in Peripheral Blood of Breast Cancer Patients, Thesis submitted for the degree of Master of Science in Molecular and Cellular Biology. Johns Hopkins University, Baltimore, Maryland (2014).
Torrano et al., Vesicle-MaNiA: extracellular vesicles in liquid biopsy and cancer, Curr. Opin. Pharmacol., 29:47-53 (2016).
Trigg et al., Factors that influence quality and yield of circulating-free DNA: a systematic review of the methodology literature, Heliyon, 4(7):e00699 (2018).
Truett et al., Efficacy of cyto-chex blood preservative for delayed manual CD4 testing using dynal T4 quant CD4 test among HIV-infected persons in zambia, J. Acquir Immune Defic Syndr., 41(2):168-174 (2006).
Tsui et al., Stability of endogenous and added RNA in blood specimens, serum, and plasma, Clin. Chem., 48:1647-1653 (2002).
Turpen et al., A reagent for stabilizing blood samples, American Clinical Laboratory, 15(8):30-31 (1996).
Tynan et al., Application of risk score analysis to low-coverage whole genome sequencing data for the noninvasive detection of trisomy 21, trisomy 18, and trisomy 13, Prenatal diagnosis, 36(1):56-62 (2016).
U.S. Provisional Application filed on Feb. 3, 2017, by Noble et al., U.S. Appl. No. 62/454,451.

(56) References Cited

OTHER PUBLICATIONS

U.S. Provisional Application filed on Feb. 3, 2017, by Noble et al., U.S. Appl. No. 62/454,460.
International Application No. PCT/US2018/056747, International Search Report and Written Opinion, mailed Dec. 17, 2018.
International Application No. PCT/US2018/056747, International Preliminary Report on Patentability, mailed Apr. 30, 2020.
International Application No. PCT/US2010/023859, International Search Report and Written Opinion, filed Feb. 11, 2010.
International Application No. PCT/US2010/55815, International Search Report and Written Opinion, filed Nov. 8, 2010.
International Application No. PCT/US2013/025912, International Preliminary Report on Patentability, mailed Apr. 25, 2014.
International Application No. PCT/US2013/025912, Written Opinion of the International Preliminary Examining Authority, mailed Jan. 24, 2014.
International Application No. PCT/US2014/047551, International Preliminary Report on Patentability, mailed Dec. 10, 2015.
International Application No. PCT/US2014/047551, International Search Report & Written Opinion, mailed Oct. 23, 2014.
Irie et al., Cyclodextrin-induced hemolysis and shape changes of human erythrocytes in vitro, J. Pharmacobiodyn, 5(9):741-744 (1982).
Ishizawa et al., Simple procedure of DNA isolation from human serum, Nucleic Acids Research, 19(20):5792 (1991).
Janse et al., Chapter 18 Flow Cytometry in Malaria Detection, Methods in Cell Biol., 42:295-318 (1994).
Jensen et al., High-throughput massively parallel sequencing for fetal aneuploidy detection from maternal plasma, PloS One, 8(3):e57381 (2013).
Jeon et al., The feasibility study of non-invasive fetal trisomy 18 and detection with semiconductor sequencing platform, PLoS One, 9(10):e110240 (2014).
Jodal et al., Investigation of the hemolytic effect of the cyclodextrin derivatives, Proceedings of the Fourth International Symposium on Cyclodextrins, 421-425, (1988).
Jundi et al., Streck cell preservative(Trademark) preserves fine needle aspiration samples for immunophenotyping by flow cytometry, Streck, 1-3 (2021).
Juneau et al., Microarray-based cell-free DNA analysis improves noninvasive prenatal testing, Fetal Diagnosis and Therapy, 36(4):282-6 (2014).
Jung et al., Changes in concentration of DNA in serum and plasma during storage of blood samples, Clin. Chem., 49 6 Pt 1:1028-1029 (2003).
Kadam et al., Quantitative measurement of cell-free plasma DNA and applications for detecting tumor genetic variation and promoter methylation in a clinical setting, The Journal of Molecular Diagnostics, 14(4):346-56 (2012).
Kagan et al., A Sample Preparation and Analysis System for Indentifieation of Circulating Tumor Cells, Journal of Clinical Ligand Assay, 25(1):104-110 (2002).
Kania et al., Urinary proteases degrade albumin: implications for measurement of albuminuria in stored samples, Annals of Clinical Biochemistry, 47:151-157 (2010).
Kashiwasaki et al., Influence of upper and lower thermoneitral room temperatures (20 ° C and 25° C) on fasting and post-prandial resting metabolism under different outdoor temperatures, European Journal of Clinical Nutrition, 44:405-413 (1990).
Katz et al., Mass-Volume Equivalents of Common Chemical Solids, Available at <http://www.chymist.com/Mass-volume%20equivalents.pdf>. 4 pages (2007).
Keller et al., Sources to Variability in Circulating Human miRNA Signatures, RNA Biol., 14(12):1791-1798 (2017).
Kelly et al., Circulating microRNA as a biomarker of human growth hormone administration to patients, 6(3):234-8 (2014).
Khosrotehrani et al., Fetal cell-free DNA circulates in the plasma of pregnant mice: relevance for animal models of fetomaternal trafficking, Human reproduction, 19(11):2460-2464 (2004).
Kidess et al., Mutation profiling of tumor DNA from plasma and tumor tissue of colorectal cancer patients with a novel, high-sensitivity multiplexed mutation detection platform, Oncotarget, 6(4):2549-2561 (2015).
Kidess-Sigal et al., Enumeration and targeted analysis of KRAS, BRAF and PIK3CA mutations in CTCs captured by a label-free platform: comparison to ctDNA and tissue in metastatic colorectal cancer, Oncotarget, 7(51):85349-85364 (2016).
Kirkizlar et al., Detection of Clonal and Subclonal Copy-Number Variants in Cell-Free DNA from Patients with Breast Cancer Using a Massively Multiplexed PCR Methodology, Translational oncology, 8(5):407-16 (2015).
Kodym et al., Determination of radiation-induced DNA strand breaks in individual cells by non-radioactive labelling of 3' OH ends, Int. J. Radiat. Biol., 68(2):133-139 (1995).
Kotsopoulou et al., Non-invasive prenatal testing (NIPT): limitations on the way to become diagnosis, Diagnosis, 2(3):141-158 (2015).
Kreuzer et al., Highly Sensitive and specific Fluorescence Reverse Transcription-PCR Assay for the Pseudogene-free Detection of β-actin Transcripts as Quantitative Reference, Clinical Chemistry, 45(2):297-300 (1999).
Krol et al., Detection of circulating tumour cell clusters in human glioblastoma, Br. J. Cancer, 119(4):487-491 (2018).
Kwee et al., Measurement of Circulating Cell-Free DNA in Relation to 18F-Fluorocholine PET/CT Imaging in Chemotherapy-Treated Advanced Prostate Cancer, Clinical and Translational Science, 5(1):65-70 (2012).
Lambert et al., Male microchimerism in healthy women and women with scleroderma: cells or circulating DNA? A quantitative answer, Blood 100(8):2845-2851 (2002).
Lambert-Messerlian et al., Feasibility of using plasma rather than serum in first and second trimester multiple marker Down's syndrome screening, Journal of medical screening, 19(4):164-70 (2012).
Lanman et al., Analytical and clinical validation of a digital sequencing panel for quantitative, highly accurate evaluation of cell-free circulating tumor DNA, PloS one, 10(10):e0140712 (2015).
Latifa et al., Comparative Study of Seven Commercial Kits for Human DNA Extraction from Urine Samples Suitable for DNA Biomarker-Based Public Health Studies, Journal of Biomolecular Techniques, 25(4):96-110 (2014).
Leal-Klevezas et al., Antifreeze solution improves DNA recovery by preserving the integrity of pathogen-infected blood and other tissues, Clin. Diagnostic Laboratory Immun., 7(6):945-946 (2000).
Leclercq, Interactions between cyclodextrins and cellular components: Towards greener medical applications?, Beilstein J. Org. Chem., 12:2644-62 (2016).
Lee et al., Down Syndrome and Cell-Free Fetal DNA in Archived Maternal Serum, Am. J. Obstet Gynecol, 187(5):1217-21 (2002).
Lee et al., Effect of platelet-associated virus on assays of HIV-1 in plasma, Science, 262:1585-1586 (1993).
Lee et al., Performance of Momguard, a new non-invasive prenatal testing protocol developed in Korea, Obstetrics & Gynecology Science, 58(5):340-5 (2015).
Lee et al., Quantitation of genomic DNA in plasma and serum samples: higher concentrations of genomic DNA found in serum than in plasma, Transfusion, 41:276-282 (2001).
Lee et al., Survival of Donor Leukocyte Subpopulations in Immunocompetent Transfusion Recipients: Frequent Long-Term Microchimerism in Severe Trauma Patients, Blood, 93:3127-3139 (1999).
Lee et al., The importance of standardization on analyzing circulating RNA, Mol. Diagn. Ther., 21(3):259-268 (2017).
Lehmann et al., Characterization and chemistry of imidazolidinyl urea and diazolidinyl urea, Contact Dermatitis, 54(1):50-58 (2006).
Lench et al., The clinical implementation of non-invasive prenatal diagnosis for single-gene disorders: challenges and progress made, Prenat. Diagn., 33(6):555-62 (2013).
Lewis et al., Detecting cancer biomarkers in blood: challenges for new molecular diagnostic and point-of-care tests using cell-free nucleic acids, Expert Rev. Mol. Diagn., 15(9):1187-200 (2015).

(56) References Cited

OTHER PUBLICATIONS

Li, et al., Detection of Paternally Inherited Fetal Point Mutations for 13-Thalassemia Using Size-Fractionated Cell-Free DNA in Maternal Plasma, JAMA., 293(7):843-849 (2005).

Liao et al., Noninvasive prenatal diagnosis of common aneuploidies by semiconductor sequencing, Proceedings of the National Academy of Sciences, 111(20):7415-20 (2014).

Uekama et al., Protective effects of cyclodextrins on drug-induced hemolysis in vitro, J. Pharmacobiodyn., 4(2):142-4 (1981).

US FDA, Draft Guidance for Industry: Pre-Storage Leukocyte Reduction of Whole Blood and Blood Components Intended for Transfusion, Vaccines, Blood & Biologics, available at: www.fda.gov/biologicsbloodvaccines/guidancecomplianceregulatoryinformation/guidance/blood/ucm076769.htm (2011).

Utting et al., Detection of tumor genetic alterations of bladder carcinomas in body fluids depends on sample treatment before DNA isolation, 906:67-71 (2000).

Van et al., An integrative approach for building personalized gene regulatory networks for precision medicine, Genome. Med., 10(1):96 (2018).

Vandenberghe et al., Non-invasive detection of genomic imbalances in Hodgkin/Reed-Sternberg cells in early and advanced stage Hodgkin's lymphoma by sequencing of circulating cell-free DNA: a technical proof-of-principle study, The Lancet Haematology, 2(2):e55-65 (2015).

Veldore et al., Validation of liquid biopsy: plasma cell-free DNA testing in clinical management of advanced non-small cell lung cancer, Lung Cancer: Targets and Therapy, 9:1-11 (2018).

Verweij et al., European Non-Invasive Trisomy Evaluation (EU-NITE) study: a multicenter prospective cohort study for non-invasive fetal trisomy 21 testing, Prenatal Diagnosis, 33(10):996-1001 (2013).

Vu et al., Genotyping for DQAI and PM loci in urine using PCR-based amplification: Effects of sample volume, storage temperature, preservatives, and aging on DNA extraction and typing, Forensic Science International, 102(1):23-34 (1999).

Wagner, Free DNA—new potential analyte in clinical laboratory diagnostics, Biochem Med (Zagreb), 22(1):24-38 (2012).

Wang et al., Gestational age and maternal weight effects on fetal cell-free DNA in maternal plasma, Prenatal diagnosis, 33(7):662-6 (2013).

Wang et al., Exploring Glycan Markers for Immunotyping and Precision-targeting of Breast Circulating Tumor Cells, Archives of medical research, 46(8):642-50 (2015).

Wang et al., Lipoprotient Lipase: from gene to obesity, Am. J. Physiol. Endocrinol. Met., 297(2):E271-E288 (2009).

Wang et al., Maternal mosaicism is a significant contributor to discordant sex chromosomal aneuploidies associated with noninvasive prenatal testing, Clinical chemistry, 60(1):251-9 (2014).

Wang et al., Real-time PCR evaluation of cell-free DNA subjected to various storage and shipping conditions, Genetics and Molecular Research, 14(4):12797-804 (2015).

Wang et al., Sensitive detection of mono-and polyclonal ESR1 mutations in primary tumors, metastatic lesions and cell free DNA of breast cancer patients, Clinical Cancer Research, 22(5):1130-7 (2016).

Warrino et al., Absolute count data from streck cell preservative treated cells, Streck Cell Preservative Application Note Issue 2, 320520-1, 1-2 (Date Unknown).

Warrino et al., Blood specimens stable in cyto-chex(Registered) BCT at elevated temperatures, Application Note, Issue 3, 20547-2, 1-4 (2006).

Warrino et al., Cyto-chex BCT stabilizes light scatter and cell morphology, Application Note, Issue 2, 320523-1, 1-4 (2005).

Warrino et al., Cyto-chex BCT stabilizes whole blood for seven days for immunophenotyping by flow cytometry, Application Note, Issue 1, 320517-4, 1-2 (2004).

Warrino et al., Cyto-chex(Registered) BCT allows for accurate T-cell counts by flow cytometry 14 days post sample collection, Application Note, Issue 4, 320563-1, 1-2 (Date Unknown).

Warrino et al., Cyto-Chex(Registered) blood collection tube stabilizes samples stored at elevated temperatures for flow cytometry analysis, Streck, Omaha, NE 68128, 1 (Date Unknown).

Warrino et al., Stabilization of white blood cells and immunologic markers for extended analysis using flow cytometry, Clinical Laboratory Products, 3 (Date Unknown).

Warrino et al., Stabilization of white blood cells and immunologic markers for extended analysis using flow cytometry, J. Immunol. Methods. 305:107-119 (2005).

Warrino, Cyto-chex BCT, not cyto-chex, should be used for preservation of CD4 cell counts, JAIDS., 43(4):503-504 (2006).

Weeks, How one laboratory reduced weekend flow cytometry staffing, Clinical Lab Products, 1-4 (2003).

Weisz et al., Protection of erythrocytes against hemolytic agents by cyclodextrin polysulfate, Biochem Pharmacol., 45(5):1011-6 (1993).

Werner et al., Analytical Validation and Capabilities of the Epic CTC Platform: Enrichment-Free Circulating Tumour Cell Detection and Characterization, Journal of Circulating Biomarkers, 4:3 (2015).

What are the regulatory Definitions for "Ambient", "Room Temperature" and "Cold Chain" (https://www.gmp-compliance.org/gmp-news/what-are-the-regulatory-definitions-for-ambient-room-temperature-and-cold-chain) (2017).

White Owen et al., Rapid whole-blood microassay using flow cytometry for measuring neutrophil phagocytosis, J. Clin. Microbiol., 30(8):2071-2076 (1992).

Wiebe et al., Inhibition of Cell Proliferation by Glycerol, Life Sciences, 48(16):1511-7 (1991).

Wienzek-Lischka et al., Noninvasive fetal genotyping of human platelet antigen-1a using targeted massively parallel sequencing, Transfusion, 55(6 Pt 2):1538-44 (2015).

Wijk et al., Detection of apoptotic fetal cells in plasma of pregnant women, Clin. Chem., 46(5):729-731 (2000).

Willems et al., The first 3,000 non-invasi-s7e prenatal tests (NWT) with the harmony test in Belgium and the Netherlands, Facts, Views & Vision in ObGyn, 6(1):7-12 (2014).

Wolf, The nature and significance of platelet products in human plasma, Br. J. Haematol., 13(3):269-88 (1967).

Wollison et al., Blood collection in cell-stabilizing tubes does not impact germline DNA quality for pediatric patients, PLoS One, 12(12):e0188835 (2017).

Wong et al., Optimizing blood collection, transport and storage conditions for cell free DNA increases access to prenatal testing, Clin. Biochem., 46(12):1099-1104 (2013).

Wong et al., The role of physical stabilization in whole blood preservation, Sci. Rep., 6:21023 (2016).

Woolcock et al., Noninvasive prenatal testing, Australian Family Physician, 43(7):432-4 (2014).

World health organization. Diagnostic imaging and laboratory technology, Use of anticoagulants in diagnostic laboratory investigations, World health organization, (?2002).

Yee et al., A novel approach for next-generation sequencing of circulating tumor cells, Mol. Genet. Genomic Med., 4(4):395-406 (2016).

Yoshida et al., Red blood cell storage lesion: causes and potential clinical consequences, Blood Transfus., 17(1):27-52 (2019).

Zhang et al., Detection and characterization of circulating tumour cells in multiple myeloma, J. Circ. Biomark., 5:10 (2016).

Zhang et al., Effect of Formaldehyde Treatment on the Recovery of Cell-Free Fetal DNA from Maternal Plasma at Different Processing Times, Clinica Chimica Acta., 397:60-64 (2008).

Zhang, et al., Genotyping of urinary samples stored with EDTA for forensic applications, Genetics and Molecular Research, 11(3):3007-12 (2012).

Zhao et al., Comparison of RNA-Seq by poly (A) capture, ribosomal RNA depletion, and DNA microarray for expression profiling, BMC Genomics, 15:419 (2014).

Zhao et al., Evaluation of two main RNA-seq approaches for gene quantification in clinical RNA sequencing: polyA+ selection versus rRNA depletion, Sci. Rep., 8(1):4781 (2018).

Zhong et al., Presence of mitochondrial tRNA(Leu(UUR)) A to G 3243 mutation in DNA extracted from serum and plasma of patients with type 2 diabetes mellitus, J. Clin. Pathol., 53:466-469 (2000).

(56) References Cited

OTHER PUBLICATIONS

Zhou et al., Collection, storage, preservation, and normalization of human urinary exosomes for biomarker discovery, Kidney Int., 69(8):1471-1476 (2006).
Zhou et al., Cyclodextrin functionalized polymers as drug delivery, Polymer Chemistry, 1:1552-1559 (2010).
Ziegler et al., Circulating DNA: a new diagnostic gold mine? Cancer Treat Rev., 28:255-271 (2002).
Nicolaides et al., Validation of targeted sequencing of single-nucleotide polymorphisms for non-invasive prenatal detection of aneuploidy of chromosomes 13, 18, 21, X, and Y, Prenatal Diagnosis, 33(6):575-9 (2013).
Niei et al., Shedding light on the cell biology of extracellular vesicles, Nat. Rev. Mol. Cell Biol., 19(4):213-228 (2018).
Nigam et al., Detection of fetal nucleic acid in maternal plasma: A novel noninvasive prenatal diagnostic technique, JIMSA., 25(3):199-200 (2012).
Norton et al., A new blood collection device minimizes cellular DNA release during sample storage and shipping when compared to a standard device, J. Clini. Laboratory Analysis, 27:305-311 (2013).
Norton et al., Cell-free DNA analysis for noninvasive examination of trisomy, New England Journal of Medicine, 372(17):1589-97 (2015).
Norton et al., Non-Invasive Chromosomal Evaluation (NICE) Study: results of a multicenter prospective cohort study for detection of fetal trisomy 21 and trisomy 18, American Journal of Obstetrics and Gynecology, 207(2):137-e1 (2012).
Notice of Opposition to a European patent dated Apr. 24, 2019, received from the European Patent Office Application No. 02761478.3.
Novaro, American Association for Cancer Research; 93rd Annual Meeting; Apr. 6-10, 2002; San Francisco, California; 43 (2002).
O'Leary et al., The importance of fixation procedures on DNA template and its suitability for solution-phase polymerase chain reaction and PCR in situ hybridization, Histochemical Journal, 26:337-346 (1994).
Oh et al., Damage to red blood cells during whole blood storage, J. Trauma Acute Care Surg., 89(2):344-350 (2020).
Ohtani et al., Differential effects of alpha-, beta-and gamma-cyclodextrins on human erythrocytes, Eur. J. Biochem., 186(1-2):17-22 (1989).
Ono et al., Circulating microRNA Biomarkers as Liquid Biopsy for Cancer Patients: Pros and Cons of Current Assays, Journal of clinical medicine, 4(10):1890-907 (2015).
Opinion Concerning the Determination of Certain Formaldehyde Releasers in Cosmetic Products. The Scientific Committee on Cosmetic Product and Non-Food Products intended for Consumers, 1-9 (2002).
Palmer et al., Flow cytometric determination of residual white blood cell levels in preserved samples from leukoreduced blood products, Transfusion, 48(1):118-128 (2008).
Pan et al., Cell-free Fetal DNA Levels in Pregnancies Conceived by PIP, Human Reproduction, 20(11):3152-3156 (2005).
Parackal et al., Comparison of Roche Cell-Free DNA collection Tubes (Registered) to Streck Cell-Free DNA BCT (Registered) s for sample stability using healthy volunteers, Pract. Lab. Med., 16:e00125 (2019).
Parpart-Li et al., The effect of preservative and temperature on the analysis of circulating tumor DNA, Clinical Cancer Research, 23(10):2471-2477 (2017).
Passage from confidential document, Streck, Inc. Cell-Free DCA BCT 510(k) Premarket Notification, Sep. 19, 2012.
Patterson et al., Fixation for in situ molecular analysis. B.K. Patterson (ed.), Techniques in quantification and localization of gene expression, 23-34 (2000).
Perakis et al., Emerging concepts in liquid biopsies, BMC Med., 15(1):75 (2017).
Persico et al., Cell-free DNA testing in the maternal blood in high-risk pregnancies after first trimester combined screening, Prenatal Diagnosis, 36(3):232-6 (2016).

Pertl et al., Detection of male and female fetal DNA in maternal plasma by multiplex fluorescent polymerase chain reaction amplification of short tandem repeats, Hum. Genet., 106:45-49 (2000).
Pertl et al., Fetal DNA in Maternal Plasma: Emerging Clinical Applications, by The American College of Obstetricians and Gynecologists, 98:483-490 (2001).
Phillips et al., Optical quantification of cellular mass, volume and density of circulating tumor cells identified in an ovarian cancer patient, Front. Oncol., 2:72 (2012).
Phillips et al., Quantification of cellular volume and sub-cellular density fluctuations: comparison of normal peripheral blood cells and circulating tumor cells identified in a breast cancer patient, Front. Oncol., 2:96 (2012).
Pietrzak-Johnston et al., Evaluation of commercially available preservatives for laboratory detection of helminths and protozoa in human fecal specimens, J. Clin. Microbiology, 38(5):1959-1964 (2000).
Pinzani et al., Circulating nucleic acids in cancer and pregnancy, Methods: A Companion to Methods in Enzymology, 40(4):302-307 (2010).
Punnoose et al., PTEN loss in circulating tumour cells correlates with PTEN loss in fresh tumour tissue from castration-resistant prostate cancer patients, British Journal of Cancer, 113(8):1225-33 (2015).
Puren et al., Laboratory operations, specimen processing, and handling for viral load testing and surveillance, Journal of Infectious Diseases, 201(supp 1):S27-S36 (2010).
Qin et al., Evaluation of a single spin protocol for plasma DNA isolation from blood collected & stored in cell-free DNA BCT, Annual Meeting of American College of Medical Genetics and Genomics (2016).
Qin et al., Stabilization of cfDNA in Urine Using a Preservative Reagent During Sample Processing, Transport, and Storage, Biofluid Biopsies & High-Value Diagnostics Nov. 16-17 and Molecular Medicine Tri-Conference February, held in Boston, (2015).
Quezada et al., Fetal fraction of cell-free DNA in maternal plasma in the prediction of spontaneous preterm delivery, Ultrasound in Obstetrics & Gynecology, 45(1):101-5 (2015).
Quezada et al., Screening for trisomies 21; 18 and 13 by cell-free DNA analysis of maternal blood at 10-11 weeks' gestation and the combined test at 11-13 weeks, Ultrasound in Obstetrics & Gynecology, 45(1):36-41 (2015).
Rait et al., Conversions of formaldehyde-modified 2'-deoxyadenosine 5'-monophosphate in conditions modeling formalin-fixed tissue dehydration, J. Histochem Cytochem 54(3):301-310 (2006).
Rajewski et al., Pharmaceutical applications of cyclodextrins. 2. In vivo drug delivery, J. Pharm. Sci., 85(11):1142-1169 (1996).
Ramirez et al., Technical challenges of working with extracellular vesicles, Nanoscale, 10:881-906 (2018).
Raposo et al., Extracellular vesicles: exosomes, microvesicles, and friends, J. Cell Biol., 200(4):373-83 (2013).
Raptis et al., Quantitation and characterization of plasma DNA in normals and patients with systemic lupus erythematosus, J. Clin. Invest., 66:1391-1399 (1980).
Rintu et al., MRCH, Does formaldehyde increase cell free DNA in maternal plasma specimens?, Laboratory Med., 47(4):286-292 (2016).
Risberg et al., Effects of collection and processing procedures on plasma circulating cell-free DNA from cancer patients, J. Mol. Diagn., 20(6):883-892 (2018).
Risberg, Establishment of PCR based methods for detection of ctDNA in blood, Thesis submitted for the Master's degree in Biomedicine. Oslo University Hospital, Institute for Cancer Research, Department of Genetics and Oslo and Akershus University College of Applied Sciences, (2013).
RNAlater product information, Sigma-aldrich technical bulletin, (2016).
Roche product alert notice—AA-harmony test-QN-SEQ-2017-003 (2017).
Rodriguez-Lee et al., Effect of blood collection tube type and time to processing on the enumeration and high-content characterization of circulating tumor cells using the high-definition single-cell assay, Arch. Pathol. Lab. Med., 142(2):198-207 (2017).

(56) References Cited

OTHER PUBLICATIONS

Rossi et al., Promises and Pitfalls of Using Liquid Biopsy for Precision Medicine, Cancer Res., 79(11):2798-2804 (2019).
Ruiz et al., Limited genomic heterogeneity of circulating melanoma cells in advanced stage patients, Physical Biology, 12(1):016008 (2015).
Rykova et al., Concentrations of Circulating RNA from Healthy Donors and Cancer Patients Estimated by Different Method, Ann. N.Y. Acad. Sci., 1075:328-333 (2006).
Sacher et al., Prospective validation of rapid plasma genotyping for the detection of EGFR and KRAS mutations in advanced lung cancer, JAMA Oncol., 2(8):1014-22 (2016).
Salvianti et al., Single circulating tumor cell sequencing as an advanced tool in cancer management, Expert review of molecular diagnostics, 27:1-3 (2015).
Anonymous: "Streck Streck ARM-D kits", 2017, XP055413636.
Yamamoto et al., Cross-linking and gel formation of water-soluble lysine polypeptides. An insolubilization model reaction for adhesive proteins, International J. Biological Macromolecules, 14(2):66-72 (1992).
Ahmad et al., Proteomics in Diagnosis: Past, Present and Future, J. Proteomics and Genomics, 1(1):1-10 (2014).
Almazi et al., Cell-Free DNA Blood Collection Tubes Are Appropriate for Clinical Proteomics: A Demonstration in Colorectal Cancer, Proteomics Clin. Applications, 12(3):e1700121 (2018).
Bryk et al., Quantitative Analysis of Human Red Blood Cell Proteome, J. Proteome Res., 16:2752-2761 (2017).
Callister et al., Normalization approaches for removing systematic biases associated with mass spectrometry and label-free proteomics, J. Proteome Res., 5(2):277-86 (2006).
Doyle et al., Plasma concentrations of platelet-specific proteins correlated with platelet survival, Blood J., 55(1):82-84 (1980).
Fauvelle et al., Mechanism of a-Cyclodextrin-Induced Hemolysis. 1. The Two-Step Extraction of Phosphatidylinositol from the Membrane, Journal of Pharmaceutical Sciences, 86(8): 935-943(1997).
Geyer et al., Plasma Proteome Profiling to Assess Human Health and Disease, Cell Systems, 2:185-195 (2016).
International Application No. PCT/US2021/039870, International Preliminary Report on Patentability, mailed Jan. 12, 2023.
International Application No. PCT/US2021/039870, International Search Report and Written Opinion, mailed Oct. 21, 2021.
Keusch et al., Role of opsonins in clinical response to granulocyte transfusion in granulocytopenic patients, American Journal of Medicine, 73(4) : 552-563(1992).
Kleinman et al., Human lymphocyte subpopulations identified by bacterial adherence are functionally different, Cellular Immunology, 48(1):43-51(1979).
Liu et al., Enhanced Detection of Low-Abundance Human Plasma Proteins by Integrating Polyethylene Glycol Fractionation and Immunoaffinity Depletion, PLOS One, 11(11):e0166306 (2016).
Norton et al., A stabilizing reagent prevents cell-free DNA contamination by cellular DNA in plasma during blood sample storage and shipping as determined by digital PCR, Clin. Biochem., 46:1561-1565 (2013).
Pasini et al., In-depth analysis of the membrane and cytosolic proteome of red blood cells, Blood, 108(3):791-801 (2006).
Rivera et al., Bacillus anthracis produces membrane-derived vesicles containing biologically active toxins, Proc. Natl. Acad. Sci. U. S. A., 107(44):19002-19007(2010).
Roka et al., Evaluation of the Cytotoxicity of (Alpha)-Cyclodextrin Derivatives on the Caco-2 Cell Line and Human Erythrocytes, Molecules, 20(11):20269-85 (2015).
Senzel et al., The platelet proteome, Curr. Opin. Hematol., 16(5):329-333 (2009).
Tsai et al., LC-MS/MS-based serum proteomics for identification of candidate biomarkers for hepatocellular carcinoma, Proteomics, 15(13):2369-2381 (2015).
Valenzeno et al., Measurement of cell lysis by light scattering, Photochemistry and Photobiology, 42(3):335-339 (1985).

\* cited by examiner

COMPOSITIONS FOR HEMOLYSIS AND COAGULATION REGULATION AND STABILIZATION OF EXTRACELLULAR VESICLES

CROSS-REFERENCE TO RELATED APPLICATION

This application is a U.S. National Phase of International Application No. PCT/US2018/056747, filed Oct. 19, 2018, which claims the benefit of U.S. Provisional Application Ser. No. 62/574,515, filed Oct. 19, 2017, the disclosure of which is incorporated by reference in its entirety.

FIELD

The present teachings relate to a blood sample regulation composition. More particularly, the present teachings relate to a composition for regulating mechanisms in a blood sample so that components within the blood sample maintain sufficient integrity for downstream testing for a variety of diagnostic indicators.

BACKGROUND

The advent of liquid biopsy (e.g., the analysis of blood or other liquid samples from the body) has revolutionized prenatal medicine and cancer diagnostics. It is now possible to isolate and analyze circulating DNA (cfDNA or cell-free DNA) (e.g., fetal or cancer), cell-free RNA, and circulating tumor cells from a patient blood sample. As analytical capabilities advance, a necessity for liquid biopsy assays is that associated pre-analytical variables be considered so that downstream results are maximized in terms of sensitivity and specificity. One of the most critical pre-analytical variables related to liquid biopsy sample collection is cellular and nucleic acid stabilization, especially considering the significant lag time associated with these samples reaching the reference laboratory. Whole blood samples are the most efficient patient samples for liquid biopsy studies, however, they are limited by multiple lag time factors. Most important among these are the fragility of white blood cells and erythrocytes/reticulocytes. Specifically, blood storage results in time-dependent release of genomic DNA from apoptotic white blood cells and cellular RNA from both deteriorating white blood cells and reticulocytes. For PCR-based liquid biopsy assays, non-specific increases in cell-free RNA and DNA risk diluting out the target transcripts (e.g., mutated oncogene DNA, fetal DNA, etc.).

While multiple commercial options for nucleic acid stabilization in whole blood exist, these are intended for stabilizing either DNA or RNA, but not both simultaneously. Collection tubes specific for stabilizing cell-free DNA include CELL-FREE DNA BCT® (Streck), ccfDNA PAXgene (Qiagen), LBGard (Biomatrica), and Cell-Free DNA (Roche). These tubes are described as preventing DNA release from apoptotic white blood cells and thus maintain time-of-draw plasma cell-free DNA levels out to 7-14 days post collection. Collection tubes intended for RNA analysis include PAXgene Blood RNA (Qiagen), RNAGard (Biomatrica), and Tempus Blood RNA (Thermo Sci.). A pitfall with the available RNA tubes is the fact that they are based on the complete lysis of the collected blood sample and thus a resulting overwhelming excess of red blood cell-specific transcripts (e.g., Globin α and β mRNA). Subsequent sample treatments are therefore required to deplete globin and ribosomal RNA and enrich the informative target mRNA pool. The lone non-lysing RNA blood collection tube on the market is the CELL-FREE RNA BCT® from Streck. A tight temperature use range is required for this tube and importantly, it is intended only for RNA stabilization. A blood collection tube that efficiently stabilizes both circulating RNA and DNA has not yet been reported.

It would be desirable to provide a collection device and composition located therein that is based on an anticoagulant formulation that both prevents blood coagulation and maintains erythrocyte mean cell volume (MCV) in an effort to minimize hemolysis. The composition would preferably stabilize the white blood cell component thereby blocking release and excessive accumulation of DNA within plasma. The composition would further act as an erythrocyte protectant that maintains red blood cell structural integrity and prevents release of membrane vesicles as a function of storage age. This is critical because circulating or cell-free RNA is encapsulated in membrane vesicles, including microvesicles and extracellular vesicles (including but not limited to exosomes). A desirable composition would maintain sample stability and integrity for a minimum of 6 days at a broad temperature range. Plasma concentrations of cfDNA and membrane vesicles, and thus cfRNA, would ideally substantially maintain draw time concentrations.

SUMMARY

The present teachings provide a composition that maintains erythrocyte MCV, substantially prevents white blood cell lysis, and substantially prevents release of extracellular membrane vesicles (e.g., exosomes, ectosomes, and the like). The methods provided herein are intended to stabilize white blood cells and erythrocytes, thereby substantially preventing the release of nucleic acids and membrane vesicles from cells in a biological sample. The composition of the present disclosure is particularly suited for use as a biological sample stabilization and regulation agent for downstream analysis via immunoassay, polymerase chain reaction, next generation sequencing and/or others.

The composition may comprise one or more components capable of releasing an aldehyde, one or more anticoagulants or chelating agents, and one or more polysaccharides. The composition may have a pH of from about 4 to about 6.

The composition may include one or more amines. The composition may include a sodium citrate composition. The composition may include one or more formaldehyde donors. The composition may include ethylenediaminetetraacetic acid or a salt thereof. The composition may include a transcription inhibitor. The composition may include one or any combination of Actinomycin D, alpha-Amanitin, Flavopiridol, DRP (5,6-dichloro-1-β-D-ribofuranosyl-1H-benzimidazole), and triptolide. The composition may include formaldehyde. The composition may be substantially free of any separately added formaldehyde. The composition may be substantially free of ethylenediaminetetraacetic acid. The composition may be substantially free of sodium heparin. The polysaccharide may be selected from starch, cellulose, glycogen, or any combination thereof.

The one or more components capable of releasing an aldehyde may be selected from diazolidinyl urea, imidazolidinyl urea, 1,3,5-tris(hydroxyethyl)-s-triazine, oxazolidine, 1,3-bis(hydroxymethyl)-5,5-dimethylimidazolidine-2,4-dione, quaternium-15, DMDM hydantoin, 2-bromo-2-nitropropane-1,3-diol, 5-bromo-5-nitro-1,3-dioxane, tris(hydroxymethyl) nitromethane, hydroxymethylglycinate, polyquaternium, or combinations thereof. The composition may include imidazolidinyl urea. The composition may include imidazolidinyl urea and may be substantially free of any other components capable of releasing an aldehyde. The composition may include diazolidinyl urea. The composition may include both imidazolidinyl urea and diazolidinyl urea. The composition may include 2-bromo-2-nitropropane-1,3-diol.

The composition may include from about 0.1% by volume to about 1% by volume of the one or more polysaccharides. The amount of formaldehyde present after sample collection may be from about 10 ppm to about 10,000 ppm.

The amine, if present, may quench available free aldehyde. Sample stability may be maintained for a minimum of 6 days at a temperature range of from about 4° C. to about 50° C. In further embodiments, sample stability is maintained for a minimum of 6 days at a temperature range of from about 2° C. to about 50° C., or from about 2° C. to about 37° C. Plasma concentrations of cfDNA and extracellular vesicles, and cfRNA, are substantially similar to draw time concentrations. Erythrocyte MCV may be maintained, white blood cell lysis may be substantially prevented, and release of extracellular vesicles (e.g., exosomes) may be substantially prevented. White blood cells may be substantially stabilized so that the number of exosomes recovered at day 4 and day 6, and possibly beyond post blood draw is substantially similar to the exosome population present at the time of blood draw. The cellular morphology and surface antigen expression may be maintained so that immunophenotyping of white blood cells by flow cytometry is enabled.

Stabilization and isolation of circulating tumor cells (CTCs) and tumor debris may also be facilitated. The testing of multiple components within a biological sample, especially when more than one blood component may be analyzed to identify indicators of the presence of a condition or disease, the severity of a disease or the success or failure of a treatment for a disease is also facilitated.

The teachings described herein further provide for a method of use of the composition described herein for stabilizing white blood cells and erythrocytes to substantially prevent the release of nucleic acids and extracellular vesicles from within cells in a biological sample.

The teachings herein further provide for a method of use of the composition described herein including as a biological sample stabilization and regulation agent for downstream analysis via immunoassay, polymerase chain reaction, next generation sequencing and/or others. The methods described herein may also include treating a single blood sample with the composition and isolating more than one of DNA, RNA, extracellular vesicles, circulating tumor cells, circulating rare cells, and proteins from the sample.

The teachings herein further provide for use of the composition described herein to isolate both DNA and RNA from a blood sample. The teachings herein further provide for use of the composition described herein to isolate extracellular vesicles from a blood sample. The teachings herein further provide for use of the composition described herein to isolate circulating tumor cells/tumor debris.

In some aspects, the disclosure provides a composition comprising: (i) a component capable of releasing an aldehyde; (ii) an anticoagulant; and (iii) cyclodextrin or a functionalized derivative thereof. In some embodiments, the component capable of releasing an aldehyde is diazolidinyl urea, imidazolidinyl urea, 1,3,5-tris(hydroxyethyl)-s-triazine, oxazolidine, 1,3-bis(hydroxymethyl)-5,5-dimethylimidazolidine-2,4-dione, quaternium-15, DMDM hydantoin, 2-bromo-2-nitropropane-1,3-diol, 5-bromo-5-nitro-1,3-dioxane, tris(hydroxymethyl) nitromethane, hydroxymethylglycinate, polyquaternium, or a combination thereof. In some embodiments, the component capable of releasing an aldehyde is imidazolidinyl urea. In further embodiments, the component capable of releasing an aldehyde is diazolidinyl urea. In still further embodiments, the component capable of releasing an aldehyde comprises imidazolidinyl urea and diazolidinyl urea. In some embodiments, the anticoagulant is a citrate-based anticoagulant comprising citrate and dextrose. In further embodiments, the citrate-based anticoagulant is anticoagulant citrate dextrose-A (ACD-A), anticoagulant citrate dextrose-B (ACD-B), or citrate-phosphate-dextrose-adenine (CPDA). In some embodiments, the citrate-based anticoagulant is present at a concentration of from about 0.75% to about 4%. In still further embodiments, the anticoagulant comprises citric acid, trisodium citrate, and dextrose. In some embodiments, the dextrose is present at a concentration of from about 2% to about 20%. In further embodiments, citrate ion concentration is from about 200 mM to about 500 mM. In some embodiments, the citric acid is present at a concentration of from about 0.5% to about 4%. In further embodiments, the trisodium citrate is present at a concentration of from about 3% to about 15%.

In some embodiments, the component capable of releasing an aldehyde is present at a concentration of from about 10% to about 40%. In further embodiments, the cyclodextrin is α-cyclodextrin or a functionalized derivative thereof. In some embodiments, the α-cyclodextrin is present at a concentration of from about 0.75% to about 4%.

In some embodiments, the composition further comprises formaldehyde. In further embodiments, the composition is free of separately added formaldehyde.

In further embodiments, sample stability is maintained for a minimum of 1 day at a temperature range of from about 2° C. to about 37° C. In some embodiments, sample stability is maintained from about 1 and up to 8 days at a temperature range of from about 2° C. to about 37° C.

In some aspects, the disclosure provides a method of inhibiting lysis of a cell comprising contacting the cell with a composition of the disclosure, wherein the inhibiting prevents release of nucleic acid and/or an extracellular vesicle from the cell. In some embodiments, the cell is a white blood cell. In further embodiments, the cell is a red blood cell. In some embodiments, the nucleic acid is cell free RNA (cfRNA), cell free DNA (cfDNA), cellular RNA, or cellular DNA. In some embodiments, lysis is inhibited for at least about 24 hours. In further embodiments, lysis is inhibited by at least 2 days, or at least 3 days, or at least 4 days. In still further embodiments, a method of the disclosure further comprises maintaining the cell for at least about 24 hours and then isolating the nucleic acid from the cell. In some embodiments, the cell is maintained at room temperature.

In some aspects, the disclosure provides a composition according to the disclosure for use in stabilizing a cell, characterized in that the use comprises contacting the cell with the composition, wherein the contacting prevents release of nucleic acid and/or an extracellular vesicle from the cell. In some embodiments, the cell is a white blood cell. In further embodiments, the cell is a red blood cell. In still further embodiments, the nucleic acid is cell free RNA (cfRNA), cell free DNA (cfDNA), cellular RNA, or cellular DNA.

DETAILED DESCRIPTION

Figure 1:
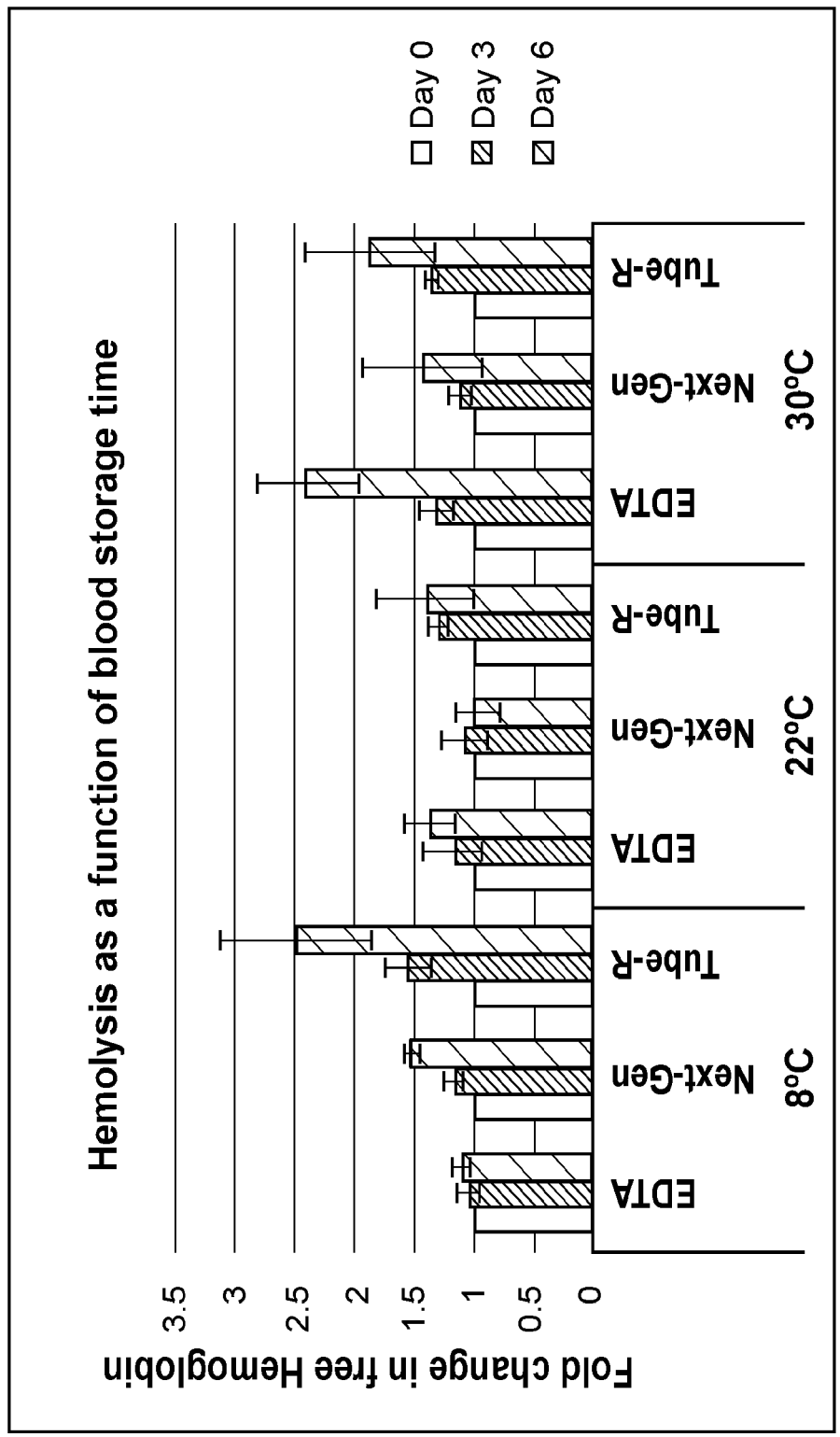
FIG. 1 is graph depicting hemolysis as a function of blood storage time utilizing three distinct formulations at three different storage temperatures.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The teachings herein are directed to blood sample regulation and cell stabilization compositions that are capable of maintaining baseline levels of extracellular vesicles; including exosomes, microvesicles, and apoptotic bodies (hereafter referred to collectively as exosomes or extracellular vesicles). Baseline levels of exosomes refers to the amount or concentration of exosomes in a blood sample immediately upon blood draw. Extracellular vesicles carry nucleic acids, thus acting as a protective envelope for cell-free nucleic acids. The amounts of extracellular vesicles and the nucleic acids in a blood sample increase over time post blood draw due to the release of vesicles from both white and red blood cells. The compositions addressed herein seek to preserve individual components including extracellular vesicles and nucleic acids and prevent cell lysis which causes intracellular material to exit from the cells and contaminate any extra-cellular material present upon blood draw. The compositions disclosed herein may substantially stabilize blood cells so that the number of extracellular vesicles recovered at day 4, and day 6 and possibly beyond post blood draw are substantially similar to the extra cellular vesicle population present at the time of blood draw. Accordingly, the concentration of cell free RNA (cfRNA), cell free DNA (cfDNA), proteins and other cellular matter which is located inside the extracellular vesicles (in addition to some cell free matter outside of the extracellular vesicles), remains the same at day 4, day 6 and possibly beyond, as it was at blood draw. Thus, the compositions of the disclosure facilitate stabilization of cfRNA, cfDNA, proteins and other cellular matter located within extracellular vesicles, genomic DNA and RNA and other RNA species (e.g., mRNA, miRNA, piRNA, siRNA, shRNA and others), allowing for downstream isolation and testing of both cell free and cellular matter (e.g., DNA and RNA from within white blood cells, circulating tumor cells (CTCs), circulating fetal cells, or other rare circulating cells). In further embodiments, the compositions of the disclosure are useful for direct and indirect extracellular vesicle analysis. The extracellular vesicle analysis is performed by, for example and without limitation, flow cytometric analysis.

A number of chemical components are commonly used in the steps of biological sample collection, biological sample treatment, and biological sample analysis. However, many of these known components are detrimental to white blood cells, red blood cells, rare circulating cells, nucleic acids, proteins, or extracellular vesicles. Further, many of these components may combine with other components to cause deleterious effects to white blood cells, red blood cells, nucleic acids, proteins, extracellular vesicles, circulating tumor cells, circulating endothelial cells, circulating progenitor cells, or circulating fetal cells. Even further, certain components are beneficial in certain concentrations, but problematic in others for a number of reasons including increase in MCV, apoptosis-induction of white blood cells, and volume needed for effectiveness. As a result, it can be extremely challenging to identify a combination of chemical components that will effectively stabilize the sample components set forth above with no detrimental effects.

Chemical components that serve and/or function as stabilizing compounds are solids in solution, thus their usability is limited by solubility and by the amount of dilution that is acceptable for downstream analysis. In order for many chemical components to be utilized as effective stabilizers, they would need to be present in an amount sufficient to stabilize the sample. Furthermore, in order to produce a direct-draw blood tube, the stabilizing composition must be present in a very small amount, so that the majority of the tube is filled with the sample. Thus, the amount of composition in the tube is ideally from about 0.02 to about 2 mL. The amount of composition in a tube may be at least about 0.5 mL or even at least about 1 mL. The amount of composition in a tube may be less than about 3.0 mL or even less than about 2.0 mL.

Often, in order for a particular chemical component to be effective, it must be present in a high enough concentration for efficacy. Unfortunately, high concentration of many chemical components may cause erythrocyte aggregation and/or rupture (as just one example), thereby increasing the MCV and creating increased hemolysis among other issues.

In an effort to balance these issues, it is necessary to identify chemical components that: (1) can be effective at low concentrations to account for the need for a relatively small amount of composition; and (2) do not react with other components in a way that damages white blood cells, erythrocytes, other rare circulating cells like tumor and fetal cells, nucleic acids, exosomes or proteins.

Additionally, the compositions according to the teachings herein may facilitate immunophenotyping of white blood cells by flow cytometry as the cellular morphology and surface antigen expression are maintained by virtue of the compositions described herein. Stabilization and isolation of circulating tumor cells and other rare circulating cells/material (e.g., circulating endothelial cells, circulating progenitor cells, circulating fetal nucleic acids in maternal blood) may also be facilitated utilizing the compositions in accordance with the present teachings. It is also possible that the compositions described herein may facilitate the testing of multiple components within a biological sample, especially when more than one blood component may be analyzed to identify indicators of the presence of a condition or disease, the severity of a disease or the success or failure of a treatment for a disease. As one non-limiting example, it may be possible to isolate CTCs stabilized with the compositions disclosed herein using mechanical isolation. This process may be followed by spinning down or centrifuging any remaining sample to collect plasma and subsequently isolate exosomes (which may include RNA) and/or cell-free DNA from the sample. Alternatively, one may isolate plasma first, followed by CTCs and WBCs isolation from the buffy coat. From the remaining cellular sample, one may isolate and analyze protein, DNA and RNA obtained from the remaining white blood cell population or from other rare cell populations including CTCs. Proteomic analysis may also be facilitated in samples treated with the compositions described herein. Thus, the compositions described herein may facilitate the ability of analysis using a single sample that is well beyond what is understood to be possible today. The ability of the compositions herein to substantially prevent hemolysis, stabilize exosomes and the associated cell-free RNA, stabilize cell-free DNA and stabilize proteins makes such multiple stage analysis possible.

Hemolysis is a common issue, specifically as it pertains to blood samples. Hemolysis can occur during one or more of the following, sample collection, sample transport, sample storage, and also during any downstream treatment of the sample. Erythrocyte lysis (e.g., hemolysis) can cause a number of challenges to cell component analysis and thus the quality of analysis improves as hemolysis is reduced. Many blood collection tubes comprise ethylenediaminetetraacetic acid (EDTA). While EDTA has been found to reduce some hemolysis, the test results identified herein (see for example FIG. 1) demonstrate the amount of hemolysis can actually be reduced by careful selection of the correct anti-coagulant. There are many anticoagulants including but limited to those based upon EDTA, heparin-based, oxalate-based, and citrate-based. The compositions herein, in various aspects, are based upon a specific type of citrate-based anticoagulant (e.g., anticoagulant citrate dextrose-A or ACD-A) due to its dual ability to show reduced hemolysis and stabilize the red blood cell membrane. Erythrocyte mean cell volume (MCV) may be reduced or stabilized with certain citrate-based anticoagulants, specifically ACD-A and ACD-B. ACD-A and ACD-B each comprise citric acid, tri sodium citrate, and dextrose. The ACD in solution A is concentrated for 8.5 milliliters of blood, while the ACD in solution B is concentrated for 6 milliliters of blood. The molarity of the citrate utilized for the compositions herein is preferably from about 0.05 M to about 0.2 M. The molarity of the citrate utilized for the compositions herein may be approximately 0.11 M. The remaining compositions for forming the compositions described herein may be diluted to have a final molarity of from about 0.0025 M to about 0.1 M.

The desire to reduce hemolysis may also require the identification of a preservative agent that will not lead to (or will minimize) erythrocyte cell lysis. It may be possible that certain preservative agents may increase the occurrence of erythrocyte lysis and thus may not be preferred preservatives for inclusion in the compositions described herein.

The concentration of the preservative agent may be selected so that white blood cell lysis is minimized. White blood cell lysis is time dependent, and most samples will eventually experience some white blood cell lysis, the amount of preservative agent should be sufficient to minimize if not eliminate white blood cell lysis for the period of time between blood draw and when samples are treated to isolate the sample components (e.g., anywhere from 24 hours to one week and possibly beyond). Thus the concentration of the preservative in the composition (prior to blood draw) may be from about 0.25% to about 2%. The concentration may be from about 2.5% to about 10%. The concentration may be about 4% to about 7%. The concentration may be from about 2.5% to about 50%. The concentration may be from about 2% to about 100%.

The concentration of any amine, if present, is likely to depend directly upon the concentration of the preservative agent. In essence the presence of the amine may act to chemically bond to a molecular component within the preservative agent. It thus may be preferable that there is sufficient amine presence in the composition so that all of the preservative agent component that is free and reactive with the amine is sufficiently reacted and thus rendered non-reactive within the sample. Such molecular bonding activity may reduce the presence of the component (which may be formaldehyde) thereby reducing any deleterious effect that reactive free formaldehyde could have on the sample components that need to be isolated an analyzed. Thus the concentration of the amine in the composition (prior to blood draw) may be from about 0.01% to about 0.2%. The concentration may be from about 0.03% to about 0.1%. The concentration may be about 0.05% to about 0.09%. The concentration may be about 0.75% to about 3.75%.

In an effort to stabilize and/or protect exosome concentration and simultaneously minimize white blood cell lysis and erythrocyte lysis, many chemicals traditionally used in biological sample collection and testing will interact with a sample in a way that damages exosomes, increases white blood cell lysis, or increases erythrocyte lysis. Many traditional chemicals interfere with the actual isolation of exosomes and nucleic acids while others lead to increased hemolysis. Further, the concentrations of some chemicals have different effects at different levels. For example, certain polysaccharides that are utilized in the compositions described herein are known to increase hemolysis; however, it was discovered that at certain lower concentrations, they act to reduce erythrocyte lysis.

The compositions herein may also include one or more transcription inhibitors. Typically, compositions for stabilizing biological samples include nuclease, metabolic, and/or protease inhibitors to block degradation of nucleic acids and/or changes in their relative concentrations (e.g., gene expression). However, the teachings herein, at least in part, are directed toward incorporating the use of transcription inhibitors instead as the intent of the formulation is to preserve baseline RNA levels. White blood cells (and other rare circulating cells) will undergo cellular signaling after blood draw, altering the RNA gene expression profile. In as short as 2 hours post draw, the RNA profile is altered. For meaningful results, maintaining base-line RNA profiles (at or close to draw time), is necessary to identify actionable targets. To do this, not only is blockage of RNA degradation needed, but inhibition of new RNA transcripts (including mRNA, microRNA, lncRNA, piRNA, YRNA, circRNA and other ncRNAs) is critical.

It is possible that in an effort to prevent erythrocyte lysis, the compositions according to the teachings herein may assist in substantially preventing any change in the size of the erythrocytes. It is also possible that this is true for the white blood cells. The ability of the compositions disclosed herein to maintain the size of the red and white blood cells may contribute to the ability to substantially prevent red and white blood cell lysis, thereby avoiding hemolysis and avoiding release of background genomic nucleic acids into the sample post-blood draw.

The compositions described herein may further act to preserve nucleic acids regardless of origin. As an example, the compositions described herein may be capable of stabilizing RNA of platelet origin. Platelets contain significant amounts of important RNA species, such as mRNA, miRNA, circRNA, and there is growing evidence that platelet mRNA expression patterns are altered in human disease. It is therefore a benefit of the compositions disclosed herein that mRNA of platelet origin is able to be isolated analyzed with RNA of other origins.

It is possible that one or more components of the compositions described herein provide efficacy to more than one facet of the sample stabilization. As one example, it is possible that the polysaccharide described herein may act to preserve the integrity of the extracellular vesicles (and thus the RNA located therein) and may also act to reduce erythrocyte lysis. Certain components (including a variety of disaccharides) were considered, but either caused or failed to mitigate hemolysis in an effective manner.

The present teachings relate generally to a method for preserving a biological sample containing blood or other biological material. The compositions described herein may contain one or more preservative agents, one or more anticoagulants or chelating agents, one or more polysaccharides, one or more amines and one or more transcription inhibitors and one or more ribonuclease inhibitors. It is possible that the composition includes two or more, three or more, four or more or even all of these components.

The preservative agent may be selected from diazolidinyl urea, imidazolidinyl urea, 1,3,5-tris(hydroxyethyl)-s-triazine, oxazolidine, 1,3-bis(hydroxymethyl)-5,5-dimethylimidazolidine-2,4-dione, quaternium-15, DMDM hydantoin, 2-bromo-2-nitropropane-1,3-diol, 5-bromo-5-nitro-1,3-dioxane, tris(hydroxymethyl) nitromethane, hydroxymethylglycinate, polyquaternium, or combinations thereof. The preservative may include a mixture of imidazolidinyl urea and diazolidinyl urea. The preservative may include imidazolidinyl urea and may be free of any other preservative agents. The preservative may include diazolidinyl urea and may be free of any other preservative agents. The preservative may include oxazolidine. The preservative may include a mixture of oxazolidine compounds. The preservative may include a bicyclic oxazolidines composition. The preservative may include triazine.

The preservative may be a derivative of uric acid. The preservative may be a reaction product of an aldehyde and a derivative of uric acid. The preservative may be selected so that at least a portion of an aldehyde (which may be formaldehyde) becomes reactive when contacted with a biological sample. However, the amount of formaldehyde present (either prior to or post sample collection) must be sufficiently low to avoid damage to any nucleic acids, extracellular vesicles or proteins present in the biological sample. The release of formaldehyde may cause an increase in the pH of the composition and/or combined composition and sample. In an effort to control the pH of the composition and/or composition and sample combination, the formaldehyde may be released in a controlled manner. The composition and/or sample may be contacted with a component for causing release of formaldehyde over time in a predetermined manner. The formaldehyde may be encapsulated as discussed herein to enable release and/or controlled release of the formaldehyde. It is also possible that the composition and/or combined composition and sample may be exposed to an elevated temperature (e.g., a temperature above ambient or room temperature) such that the increase in temperature causes release or increased release of formaldehyde (and thus an increase in pH). Alternatively, the formaldehyde may be released immediately upon contact of a formaldehyde releaser with the composition. The formaldehyde may be released upon contact of the composition with a sample. The formaldehyde releaser may be selected such that the formaldehyde is inherently released over time, without need to encapsulate the formaldehyde or to treat the composition in some way to mandate controlled release.

The composition and/or sample and composition may further include one or more byproducts of the components included within a stabilizing tube in accordance with the teachings herein. One or more of these byproducts may include an aldehyde. One or more of the byproducts may include a urea. One or more byproducts may be selected from allantoin, (4-hydroxymethyl-2,5-dioxo-imidazolidine-4-yl)-urea, (3,4-bis-hydroxymethyl-2,5-dioxo-imidazolidine-4-yl)-urea, and (3-hydroxymethyl-2,5-dioxo-imidazolidine-4-yl)-urea.

Any aldehyde present either pre or post sample collection may be in an amount below 40,000 ppm, below 30,000 ppm, below 20,000 ppm, or even below 10,000 ppm. That being said, it may be that some formaldehyde is present to effectively crosslink and stabilize one or more of the white blood cells and/or erythrocytes. Thus, the formaldehyde may be present in an amount of at least 2,000 ppm, at least 5,000 ppm, or even at least 10,000 ppm. It is possible that the amount of free formaldehyde in the composition prior to contact with a sample is up to about 0.5 weight percent, up to about 1.0 weight percent, up to about 2 weight percent, or even up to about 3 weight percent of the composition. The composition may contain less than about 20 parts per million (ppm) of an aldehyde. The composition may contain less than about 15 ppm of an aldehyde. The composition may contain less than about 10 ppm of an aldehyde. The composition may contain less than about 5 ppm of an aldehyde. The composition may contain at least about 0.1 ppm to about 20 ppm of an aldehyde. The composition may contain at least about 0.5 ppm to about 15 ppm of an aldehyde. The composition may contain at least about 1 ppm to about 10 ppm of an aldehyde.

The preservative may have a pH of at least about 4, at least about 5, or even at least about 6. The preservative may have a pH of less than 8, less than 7, or less than 6. The preservative may have a pH of from about 4 to about 6. The preservative may have a molecular weight of at least about 20 g/mol, at least about 50 g/mol, or event at least about 80 g/mol. The preservative may have a molecular weight of less than about 500 g/mol, less than about 400 g/mol, or less than about 300 g/mol.

The one or more preservative agents may be present in the composition in a concentration of about 0.5% to about 5.0% by volume. The one or more preservative agents may be present in the composition in a concentration of about 0.5% to about 1.0% by volume. The one or more preservative agents may be present in the composition in a concentration of about 5% by volume. The one or more preservative agents may be present in the composition in a concentration of about 2.5% by volume.

The pH of the composition may vary before contact with a sample and after contact with a sample. The composition may include one or more ingredients for causing the pH of the composition to range (prior to sample contact) from at least about 3, at least about 4, at least about 5, to below about 11, below about 10, or even below about 9. For example, the pH of the composition prior to contact with a sample may be from 3 to about 6. The composition may include one or more agents that are responsible for causing release of an acidic compound upon contact with a sample. The pH of the combined sample and composition may be at least about 5, at least about 6, or even at least about 7. The pH of the combined sample and composition may be below about 10, below about 9, or even below about 8.

The one or more amines may be selected from one or more of tryptophan, tyrosine, phenylalanine, glycine, ornithine and S-adenosylmethionine, aspartate, glutamine, alanine, arginine, cysteine, glutamic acid, glutamine, histidine, leucine, lysine, proline, serine, threonine, or combinations thereof. The one or more amines may be chosen based upon their reactive capabilities. As one non-limiting example, it is possible that the one or more amines be aldehyde reactive agents. For example, the aldehyde reactive agent may be selected from one or any combination of tris, lysine, glycine, urea, or a derivative (e.g., a salt and/or an ester) of either or both. The aldehyde reactive agent may be selected to react with any free formaldehyde that may be present either prior to or post sample collection. The concentration of the amines in the composition (prior to blood draw) may be from about 0.25% to about 1.5%. The concentration may be from about 0.3% to about 0.8%. The concentration may be about 0.4% to about 0.7%.

The one or more anticoagulants or chelating agents may be selected from the group consisting of ethylene diamine tetra acetic acid (EDTA) and its salts, ethylene glycol tetra acetic acid (EGTA) and its salts, hirudin, heparin, citric acid, salts of citric acid, oxalic acid, salts of oxalic acid, acid citrate dextrose (ACD), citrate, citrate-theophylline-adenosine-dipuridamole (CTAD), citrate-pyridoxalphosphate-tris, heparin-8-hydroxy-ethyl-theophylline, polyanethol sulfonate, sodium fluoride, sodium heparin, thrombin and PPACK (D-phenylalanyl-L-prolyl-L-arginine chloromethyl ketone and any combination thereof. Thus the concentration of the anticoagulant in the composition (prior to blood draw) may be from about 2.5% to about 10%. The concentration may be from about 3% to about 8%. The concentration may be about 4% to about 7%.

The one or more polysaccharides may be selected from starch, cellulose, glycogen, or combinations thereof. The one or more polysaccharides may act erythrocyte protectant agents. The one or more polysaccharides may assist in stabilizing erythrocyte membranes, such that cell lysis is slowed, minimized, substantially prevented or some combination thereof. The concentration of the polysaccharides in the composition (prior to blood draw) may be from about 0.001% to about 5.0%. The concentration may be from about 0.02% to about 3.0%. The concentration may be about 0.5% to about 2.0%.

The one or more transcription inhibitors may be selected to promote stability of one or more components within a sample. The one or more transcription inhibitors may be selected from actinomycin D, α-amanitin, triptolide, 5,6-dichloro-1-β-D-ribofuranosylbenzimidazole (DRB), flavopiridol, or any combination thereof. The concentration may be about 0.5 μM to about 500 μM.

The sample blood collection tube may include one or more enzyme inhibitors. The one or more enzyme inhibitors may be selected from the group consisting of: diethyl pyrocarbonate, ethanol, aurintricarboxylic acid (ATA), glyceraldehydes, sodium fluoride, ethylenediamine tetraacetic acid (EDTA), formamide, vanadyl-ribonucleoside complexes, macaloid, heparin, hydroxylamine-oxygen-cupric ion, bentonite, ammonium sulfate, dithiothreitol (DTT), beta-mercaptoethanol, cysteine, dithioerythritol, tris(2-carboxyethyl)phosphene hydrochloride, a divalent cation such as Mg+2, Mn+2, Zn+2, Fe+2, Ca+2, Cu+2 and any combination thereof.

The sample blood collection tube may include one or more metabolic inhibitors. The one or more metabolic inhibitors may be selected from the group consisting of: glyceraldehyde, dihydroxyacetone phosphate, glyceraldehyde 3-phosphate, 1,3-bisphosphoglycerate, 3-phosphoglycerate, 2-phosphoglycerate, phosphoenolpyruvate, pyruvate and glycerate dihydroxyacetate, sodium fluoride, $K_2C_2O_4$ and any combination thereof.

The sample blood collection tube may include one or more protease inhibitors. The one or more protease inhibitors may be selected from the group consisting of: antipain, aprotinin, chymostatin, elastatinal, phenylmethylsulfonyl fluoride (PMSF), APMSF, TLCK, TPCK, leupeptin, soybean trypsin inhibitor, indoleacetic acid (IAA), E-64, pepstatin, VdLPFFVdL, EDTA, 1,10-phenanthroline, phosphoramodon, amastatin, bestatin, diprotin A, diprotin B, alpha-2-macroglobulin, lima bean trypsin inhibitor, pancreatic protease inhibitor, egg white ovostatin, egg white cystatin, Doxycycline, Sulfasalazine, Curcumin, Homocysteine, 6-Aminocaproic acid, Doxycycline, Minacycline HCl, Nicotinamide, Chitosan, Lysine, Glyceraldehyde, Phytic Acid, b-Sitoserol, C-AMP, Poly Lysine Low MW, Biochanin A, Sulfasalazine, Demeclocycline, Chlortetracycline, Oxytetracycline, Cyclohexamide, Rifampicin, Soy Milk, Suramin, N-Butyric Acid, Penicillamine, N-Acetyl Cysteine, Benzamidine, AEBSF, and any combination thereof. The protective agent may include a phosphatase inhibitor selected from the group consisting of: calyculin A, nodularin, NIPP-1, microcystin LR, tautomycin, okadaic acid, cantharidin, microcystin LR, okadaic acid, fostriecin, tautomycin, cantharidin, endothall, nodularin, cyclosporin A, FK 506/immunophilin complexes, cypermethrin, deltamethrin, fenvalerate, bpV(phen), dephostatin, mpV(pic) DMHV, sodium orthovanadate, and any combination thereof.

The sample blood collection tube may include one or more nuclease inhibitors. The one or more nuclease inhibitors may be selected from the group consisting of: diethyl pyrocarbonate, ethanol, aurintricarboxylic acid (ATA), formamide, vanadyl-ribonucleoside complexes, macaloid, ethylenediamine tetraacetic acid (EDTA), proteinase K, heparin, hydroxylamine-oxygen-cupric ion, bentonite, ammonium sulfate, dithiothreitol (DTT), beta-mercaptoethanol, cysteine, dithioerythritol, tris(2-carboxyethyl) phosphene hydrochloride, or a divalent cation such as Mg+2, Mn+2, Zn+2, Fe+2, Ca+2, Cu+2 and any combination thereof.

The sample blood collection tube may include one or more phosphatase inhibitors. The one or more phosphatase inhibitors may be selected from the group consisting of: calyculin A, nodularin, NIPP-1, microcystin LR, tautomycin, okadaic acid, cantharidin, imidazole, microcystin LR, okadaic acid, fostriecin, tautomycin, cantharidin, endothall, nodularin, cyclosporin A, FK 506/immunophilin complexes, cypermethrin, deltamethrin, fenvalerate, bpV(phen), dephostatin, mpV(pic) DMHV, sodium orthovanadate, and any combinations thereof.

The sample blood collection tube may include bicyclic oxazolidines, DMDM hydantoin, sodium hydroxymethylglycinate, hexamethylenetetramine chloroallyl chloride, biocides, a water-soluble zinc salt, or any combination thereof. The sample blood collection tube may include a polyacrylic acid or a suitable acid having a pH ranging from about one to about seven. The sample blood collection tube may include amines, amino acids, alkyl amines, polyamines, primary amines, secondary amines, ammonium salts, or any combination thereof. The sample blood collection tube may include one or more primary amines. The sample blood collection tube may include one or more amides (e.g., butanamide). The sample collection tube may include one more apoptosis inhibitors. The sample collection tube may include one or more caspase inhibitors.

The sample blood collection tube may include one or more polymer ingredients. The polymers may include but are not limited to the following: polyvinylpyrrolidone (PVP), polyethylene glycol (PEG), and cyclodextrin.

The compositions described herein may also include additional components, including one or more of the following: Doxycycline, Polyethylene Glycol, Sulfasalazine, Polyvinylpyrrolidone, Curcumin, Magnesium Gluconate, Homocysteine, Methyl Cellulose (MC), 6-Aminocaproic acid, Ethyl Cellulose, Aprotinin, Hydroxyethyl Cellulose, Doxycycline, Hydroxypropyl Cellulose, Minocycline HCl, Dextrin, Nicotinamide, Dextran, Chitosan, Polyethylene Oxide, Lysine, Poly Ethyl Oxazoline, Glyceraldehyde, Ficolls, Phytic Acid, α-Cyclodextrin, b-Sitoserol, ß-Cyclodextrin, C-AMP, Y-Cyclodextrin, Poly Lysine, Gelatins, Biochanin A, Sugars (e.g., sucrose, mannitol, lactose, trehalose), Sulfasalazine, Hydroxypropyl Methyl Cellulose, Demeclocycline, Hydroxyethyl Methyl Cellulose, Chlortetracycline, Oxytetracycline, Cyclohexamide, Rifampicin, Soy Milk, soybean based protease inhibitor, Suramin, N-Butyric Acid, Penicillamine, N-Acetyl Cysteine, Benzamidine, AEBSF, Alpha-2 Macroglobulin, or combinations thereof. It is contemplated that one or more of the foregoing compounds can be substituted for cyclodextrin in a composition of the disclosure.

The sample collection tube may include one or more surface-active agents. The one or more surface-active agents are DMSO (dimethyl sulfoxide), ethylene glycol, polyethylene glycol, glycerin, Cellosolves (ethylene glycol dimethyl ether) (phenoxyethanol), Triton X 100, Triton X 705 (non-ionic detergents), 1-methyl-2-pyrrolidinone, Tween 20, Tween 40 (non-ionic), Brij 35 (detergent), polyoxyethylene ether (Polyox), sodium cholate, ethylene oxide polymers, monensin, monactin, pentachlorophenol, 2,4 dinitrophenol, saponin, SDS (sodium dodecyl sulfate), or a combination thereof. The effects of the foregoing surface-active agents are contemplated herein to be concentration-dependent. For example and without limitation, it is contemplated that in some embodiments lower concentrations of the foregoing surface-active agents are useful for inhibiting lysis of a cell by contacting the cell with a composition of the disclosure, wherein the inhibiting prevents release of nucleic acid and/or an extracellular vesicle from the cell.

The sample collection tube may include proteins such as: biotin, albumins (egg, bovine), gelatin, and similar such compounds. The sample collection tube may include RNAse inhibitors such as: human placenta derived RNAse inhibitor, and similar such compounds. The sample collection tube may include nucleic acid stabilizers such as: guanidinium hydrochloride, polycations such as polyethylenimine, and similar such compounds. The sample collection tube may include amino acids/polypeptides such as: glutamic acid, glycine, aspartic acid, and similar such compounds. The sample collection tube may include fixatives such as: aldehydes (formaldehyde and glutaraldehyde), alcohols (ethanol, methanol), and similar such compounds. The sample collection tube may include anticoagulants such as: EDTA (Ethylene Diamine Tetra acetic acid), and similar such compounds. The sample collection tube may include ACD (Acid Citrate Dextrose), Heparin, and similar such compounds. The sample collection tube may include protease inhibitors such as: EDTA, PMSF (phenyl methyl sulfonyl fluoride), AEBSF (2-Aminoethyl benzene sulfonyl fluoride), and similar such compounds. The sample collection tube may include antioxidants/reducing agents such as: Trolox, a-tocopherol, B-mercaptoethanol, and similar such compounds. The sample collection tube may include nucleic acid dyes such as: DAPI (diamidino 2-phenylindole), propidium iodide, fluorescein diacetate, and similar such compounds. The sample collection tube may include carbohydrates such as: sugars (sucrose), cellulose, and similar such compounds. It should be appreciated that the above specific listings of compounds may contain a measure of overlap, which recognizes the sometimes-overlapping function of certain specific compounds. One of skill in the art should understand and appreciate this aspect of the disclosure.

The aldehyde reactive agent may be present in a ratio (by weight) relative to the preservative of about 1:20 to about 1:1. The aldehyde reactive agent may be present in a ratio (by weight) relative to the anticoagulant of about 1:25 to about 5:1. The preservative may be present in a ratio (by weight) relative to the anticoagulant of about 1:10 to about 15:1.

One or more of the components in the composition may be in gel form, in liquid form, in solid form, or in some combination thereof. One or more of the components of the composition may be particulated and/or may form a film on a wall of a sample collection container and/or sample testing container. One or more of the components may be lyophilized and then sprayed on one or more portions of the sample collection container. One or more of the components within the composition may be encapsulated within an encapsulant. The encapsulant may be selected to decompose or otherwise expose the encapsulated material upon contact with a sample thereby delivering the material within the encapsulant to the sample. The composition may include an inactive component such as a buffer or water.

The one or more preservative agents may be present in the composition in a concentration of about 0.5% to about 5.0% by volume. The one or more preservative agents may be present in the composition in a concentration of about 0.5% to about 1.0% by volume. The one or more preservative agents may be present in the composition in a concentration of about 0.5% by volume. The one or more preservative agents may be present in the composition in a concentration of about 0.75% by volume. The one or more preservative agents may be present in the composition in a concentration of about 1% by volume. The one or more preservative agents may be present in the composition in a concentration of about 2.5% by volume. The one or more preservative agents may be present in the composition in a concentration of about 5% by volume.

The composition may be substantially free of detergents and chaotropic agents and any or more of substances that lead to lysis of RBCs, WBCs, platelets, and other rare circulating cells. The composition may be substantially free of any or more of substances that lead to cellular activation and subsequent release of membrane vesicles including calcium ionophores and chemotherapeutic drugs. The composition may be substantially free of any or more of substances that lead to RBC hemolysis and an increase in RBC MCV including anti-malaria drugs, nitrites and heavy metals. The composition may be substantially free of any or more of substances that lead to downstream PCR inhibition including anticoagulant heparin, calcium ions, heme and hemoglobin. The composition may be substantially free of any or more of substances that lead to coagulation including thrombin, calcium ions, silica and Celite. The composition may further be substantially free of one or more of tris buffer, bovine serum albumen, polysorbate 20, sodium azide, sodium chloride, serum separator, clot activator, and gentamicin.

The biological sample may be stabilized for a period of at least three days. The biological sample may be stabilized for a period of at least five days. The biological sample may be stabilized for a period of at least seven days. Preferably, hemoglobin degradation of a biological sample including blood material is stabilized for a period of at least 5 days.

The compositions described herein may be utilized in a method which may include a step of handling the biological sample, while it remains suspended in the composition, for delivery to a remote site at which analysis of the blood material is to be performed. The method may include transport (e.g., shipping) the biological sample, while it remains suspended in the composition for delivery to a site at which analysis of the blood material is to be performed. The method may include exposing the sample during handling and/or transport to temperature fluctuations. For example, such exposure may be at temperatures from about 4° C. to about 37° C., or from about 2° C. to about 37° C. The method may include exposing the sample during handling and/or transport to temperatures up to 37° C. The remote site may be a site at which any downstream analysis of the blood material is to be performed. The site may be a site at which immunoassay or nucleic acid analysis of the blood material is to be performed.

The composition and/or the sample may be located into a sample container. The sample container may contain the composition or the composition combined with a sample in an amount of at least 0.5 ml, at least 1 ml, at least 3 ml, at least 5 ml, at least 10 ml, or even at least 20 ml. The sample container may contain the composition or the composition combined with a sample in an amount of less than 150 ml, less than 100 ml, less than 50 ml, or even less than 20 ml. The compositions described herein may be present in a direct draw blood tube. The compositions described herein may be located into any device for collecting a biological sample. The compositions described herein may be located in a sample receiving container prior to addition of the sample or may be added to the sample post-collection.

The sample container may be a tube. The sample container may be cylindrical. The sample container may be glass or may be polymeric. The sample container may have a barrier coating which may be a chemically enhanced plasma vapor deposition coating, such as is taught in U.S. Provisional Application Nos. 62/454,451 and 62/454,460, both filed on Feb. 13, 2017 and PCT Patent Publication No. WO2017/031354, the entirety of the contents of these applications being hereby incorporated by reference herein for all purposes.

The sample container may be part of a kit. The kit may include a cap or cover for the sample container so that the sample remains inside the sample container, even in the event that the sample is shipped to a test facility in the sample container.

The sample container post blood draw may contain a combination of a blood sample and formaldehyde. The sample container may contain a combination of a blood sample, anticoagulant, and formaldehyde. The sample container may contain a combination of a blood sample, formaldehyde, anticoagulant, and polysaccharide. The sample container may contain a combination of a blood sample, formaldehyde, anticoagulant, polysaccharide and transcription inhibitor. The sample container may contain a combination of a blood sample, formaldehyde, anticoagulant, polysaccharide, transcription inhibitor, and amino acid.

The method may include analyzing the biological sample for one or more indicators of a disease state. The biological sample may be an abnormal biological sample. For example, abnormal results may include altered DNA, altered RNA, and/or altered proteins and/or rare circulating cells including CTCs, circulating endothelial cells, circulating progenitor cells, and circulating fetal cells. Circulating cells may also be understood to include circulating cell components including nucleic acids.

The method may include analysis of the stabilized biological sample including blood material. The analysis may include one or more testing methods. The method may include immunoassay of the blood material and/or one or more components within the blood material (e.g., blood cells, rare cells, nucleic acids, circulating tumor cells/fragments, circulating endothelial cells, circulating progenitor cells, fetal cells in maternal blood, extracellular vesicles). The immunoassay may be selected from the group consisting of enzyme linked immunosorbent assay (ELISA), enzyme immunoassay (EIA), radioimmunoassay (RIA), counting immunoassay (CIA), fluoroimmunoassay (FIA), chemiluminescent (CLIA) and flow cytometry. The method may include nucleic acid analysis of the blood material. The nucleic acid analysis may be selected from the group consisting of genetic sequencing, polymerase chain reaction, and next generation sequencing.

The sample collection tube of the present teachings may resist adherence of the contents of the collected biomedical sample to the walls of the sample collection tube. For example, the interior surface of the blood collection tube may resist adherence to blood cells of the drawn blood sample. The blood collection tube may resistance adherence of nucleic acids (e.g., DNA) of the drawn blood sample to the walls of the tube.

The sample collection tube of the present teachings may include a tube having an enclosed base, a coextensive elongated side wall extending from the base and terminating at an open end, and defining a hollow chamber having an inner wall, the hollow chamber being configured for collecting a blood sample, at least the elongated side wall of the tube being made of a material including a thermoplastic polymeric material having a moisture barrier and low moisture absorption rate, optical transparency to enable viewing a sample within the tube and chemical resistance; and optionally a transparent silicon-containing coating on at a majority of the side wall of the tube; and an elastomeric stopper. Prior to collecting a blood sample, the hollow chamber of the tube is in an evacuated condition relative to an ambient pressure, and the hollow chamber is partially filled with a composition in an initial state selected from a solid, a liquid or a gel, the composition including an optional anticoagulant, and a preservative composition adapted for stabilizing blood cells of the blood sample for enabling isolation of a nucleic acid or a rare cell circulating in the blood sample and/or flow cytometry testing of the blood sample. The composition is capable of retaining its initial state for a period of at least one month over a temperature range of about 2° C. to about 30° C. The composition may include or the tube may be adapted to receive one or more materials for enabling isolation of a cellular or cell-free component of a blood sample. Such materials may include a protease or amino acid which may include but is not limited to proteinase K.

The blood sample collection tube may be a single use tube. The blood sample collection tube may be non-pyrogenic or endotoxin free. The blood sample collection tube may be used to collect blood samples for analytical purposes.

The blood sample collection tube is an evacuated direct draw blood collection tube which is used for stabilization and preservation. The blood sample collection tubes may be used for the stabilization and preservation of nucleic acids. For example, the blood collection tubes of present teachings may be used for non-invasive prenatal testing (NIPT) which analyzes cell-free fetal DNA circulating in maternal blood. The prenatal tests may include fetal sex determination, genetic screening for one or more chromosomal conditions (e.g., trisomy) and prenatal DNA paternity testing. The tube may be part of a kit adapted for a non-invasive testing of a maternal blood sample of a pregnant woman. The blood sample collection tubes may be used for the stabilization and preservation of circulating tumor cells and/or tumor DNA. The blood sample collection tubes may be used for flow cytometry testing and analysis. The tube may be part of a kit for detecting circulating tumor cells. The tube may be part of a kit for detecting cancer indicating nucleic acid activity in RNA and/or DNA. The tube may be part of a kit for determining the efficacy of a treatment for a disease state. The tube may be part of a kit for testing for biomarker presence or the presence of heart disease. The tube may be part of a kit for testing for transplant suitability.

Evacuated blood collection tubes typically have an expiration date. An expired tube may have a decreased vacuum, resulting in a short blood draw and leading to an improper blood to composition ratio. Thus, it is important that a blood collection tube be able to maintain a vacuum for an extended period of time. The blood collection tube of the present teachings may provide an evacuated blood collection tube which maintains a vacuum for an extended period of time (e.g. at least 24 months). Furthermore, the draw tolerance of the blood collection tube should be accurate (e.g., +/−10% of ml of the stated collection volume). It is also important that the structure of the tube, including its closure mechanism promotes maintaining the necessary pressure within the tube, despite fluctuations in the environment during tube transport. Such fluctuations may include changes in temperature, changes in air pressure, changes in humidity and other environmental factors. More specifically, the tube must remain securely closed despite decreased humidity and decreased air pressure that may occur at higher altitudes. As an example, the tube must stay sealed and maintain the required internal pressure when the environmental barometric pressure is anywhere from 400 mmHg to 800 mmHg.

The blood collection tube may be adapted for use with a stopper. The stopper may include an elastomeric material. The stopper may include a butyl rubber derivative. The stopper may include a halogenated butyl. The stopper may include bromobutyl rubber. The stopper may include pharmaceutical bromobutyl rubber. The stopper may be utilized with stopper lubricant. The stopper may be coated. The stopper may be partially coated. For example, the coating may include silicone. The stopper of the tube may include a silicone oil coating over at least a portion of its outer surface that contacts the inner wall of the tube.

The present teachings contemplate a blood collection tube assembly including the blood collection tube of the present teachings and a stopper. It is contemplated that the seal or interface of the outer wall of the cap and the inner wall of the tube is such that the moisture transmission rate is substantially reduced. It is contemplated that the seal or interface of the outer wall of the stopper and the inner wall of the tube is such that the oxygen transmission rate is substantially reduced. An effective seal should provide both a moisture barrier and a gas barrier. The present teachings provide a blood collection tube assembly in which the stopper resists pull out from the opening of the tube. The present teachings provide a blood collection assembly which provide both an effective moisture transmission barrier, thereby preventing moisture from escaping from inside of a tube filled with composition, and an effective oxygen transmission barrier, thereby preventing penetration of oxygen into the tube.

The compositions described herein may be capable of retaining their initial state for a period of at least one month over a temperature range of about 2° C. to about 30° C. when the tube is subjected to relative humidity of up to about least about 50%. The composition may be capable of retaining its initial state for a period of at least one month over a temperature range of about 2° C. to about 30° C. when the tube is subjected to relative humidity of up to about 75%.

The sample collection tube's dimensions may be about 13 mm×75 mm. The tube may have an outer diameter, as measured at the coextensive elongated side wall adjacent the open end, to length (D×L) dimension of about 13 mm×75 mm. The sample collection tube's dimensions may be about 16 mm×100 mm. The tube may have an outer diameter, as measured at the coextensive elongated side wall adjacent the open end, to length (D×L) dimension of about 16 mm×100 mm. The blood sample collection tubes may be suitable for about 2 ml to about 10 ml of blood collection. For example, a small blood collection tube may be suitable for about 2 ml of blood sample collection. For example, a large blood collection tube may be suitable for about 10 ml of blood sample collection.

The blood collection tube may include a composition fill tolerance volume of about 50 µl to about 70 µl. The blood collection tube may include a composition fill tolerance volume of about 54 µl to about 66 µl. The blood collection tube may include a composition fill tolerance volume of about 60 µl. The tube may include a composition fill tolerance volume of about 160 µl to about 220 µl. The tube may include a composition fill tolerance volume of about 180 µl. The tube may include a composition fill tolerance volume of about 200 µl. The tube may include a composition fill tolerance volume of about 200 µl to about 1,000 µl. The tube may include a composition fill tolerance volume of about 750 µl. The tube may include a composition fill by weight about 0.0600 g to about 0.0800 g. The tube may include a composition fill by weight about 0.0700 g. The tube may include a composition fill by weight of plus or minus 10% of 0.0650 g. The tube may include a composition fill by weight of plus or minus 10% of 0.0700 g. The tube may include a composition fill by weight of plus or minus 10% of 0.0750 g. The tube may include a composition fill by weight about 0.200 g to about 0.300 g. The tube may include a composition fill by weight about 0.250 g. The tube may include a composition fill by weight of plus or minus 10% of 0.225 g. The tube may include a composition fill by weight of plus or minus 10% of 0.250 g. The tube may include a composition fill by weight of plus or minus 10% of 0.275 g.

The blood collection tube may include a draw tolerance of about 3 ml to about 5 ml. The blood collection tube may include a draw tolerance of about 4 ml. The blood collection tube may include a draw tolerance of about 7 ml to about 13 ml. The blood collection tube may include a draw tolerance of about 10 ml. The blood collection tube may include a composition fill volume of about 200 µl. The blood collection tube may include a composition fill volume of about 750 µl. The blood collection tube may include a composition fill volume of about 200 µl to about 750 µl. The blood collection tube may include a composition fill volume of about 500 µl. The blood collection tube may include a composition fill volume of about 500 µl to about 750 µl. The blood collection tube may include a composition fill volume of about 1 ml. The blood collection tube may include a composition fill volume of about 500 µl to about 1 ml. The blood collection tube may include a composition fill volume of about 200 µl to about 1 ml. The blood collection tube may include a composition fill volume of about 2 ml. The blood collection tube may include a composition fill volume of about 1 ml to about 2 ml. For example, a 10 ml blood collection tube may include a composition fill volume of about 1 ml to about 2 ml. For example, a 4 ml blood collection tube may include a composition fill volume of about 1 ml to about 2 ml.

The polymeric material of the tube described herein to contain the composition may be characterized as having one or more of the following: a moisture barrier and low moisture absorption rate, purity, transparency, chemical resistance, heat resistance, and strength. The polymeric material may have one or more of the following attributes: low density, high transparency, low birefringence, extremely low water absorption, excellent water vapor barrier properties, variable heat deflection properties, high rigidity, strength and hardness, very good blood compatibility, excellent biocompatibility, very good resistance to acids and alkalis, very good electrical insulating properties, and very good processability/flowability.

The polymeric material may include a cyclic olefin. The polymeric material may include cyclic olefin copolymer (COC). The polymeric material may include a homopolymer or copolymer that includes polyethylene, polypropylene, or both. The polymeric material may include a cyclic moiety. The polymeric material may include a polyester. The polymeric material may include polyester terephthalates or polyethylene terephthalate. The polymeric material may include polycarbonates. The polymeric material may include poly(methyl methacrylate).

The polymeric material may have excellent water vapor barrier properties. The polymeric material may have a low moisture vapor transmission rate (MVTR) or water vapor transmission rate (WVTR). The moisture vapor transmission rate may be determined according conventional testing methods such as DIN 53 122. The polymeric material may have a moisture vapor transmission rate of about 0.023 g·mm/m$^2$·d to about 0.045 g·mm/m$^2$·d at 23° C. and 85% relative humidity, as measured by DIN 53 122. The polymeric material may have a moisture vapor transmission rate of about 0.023 g·mm/m$^2$·d at 23° C. and 85% relative humidity. The polymeric material may have a moisture vapor transmission rate of less than about 0.023 g·mm/m$^2$·d at 23° C. and 85% relative humidity.

The sample collection tube may include a coating. The sample collection tube may be uncoated. The sample collection tube may be a blood collection tube with a coating on the inner wall of the tube. The coating may include one or more layers. The coating may be generally transparent. The coating may include a silicon containing material.

The coating may serve one or more functions. The coating of the blood collection tube may be such that it alters one or more characteristics of the interior surface of the blood collection tube. For example, the coating may alter the surface energy of the inner walls of the tube. The coating may assist in preventing adherence of nucleic acids to the walls of the tube.

The coating, including one or more layers, may be deposited on the inner wall of the tube via any suitable mechanism. For example the coating may be deposited onto the polymeric substrate by a plasma, a spray, and/or a sputter deposition method. It may be applied by a vapor deposition method. It may be applied by a chemical deposition method. It may be applied by a physical deposition method.

The present teachings provide a blood collection tube which does not allow a composition(s) to lose moisture over time. Moisture loss can cause the stabilizing composition to become concentrated, which can potentially damage the integrity of all cells, including red blood cell lysis and produce excessive hemolysis.

The blood collection tube of the present teachings may include a composition. The tube may include a composition with one or more ingredients. The ratio of one or more ingredients of the composition may be about 5:1 to about 15:1 (e.g., 10:1). The composition may be solid. The composition may be substantially solid. The composition may be a liquid. The composition may be a gel. The composition may be a film. The composition may include an aqueous substance. The composition may include one or more agents in composition. Suitable solvents may include water, saline, dimethylsulfoxide, alcohol and any mixture thereof.

The blood collection tube of may include a blood draw volume of about 4 ml to about 10 ml. The blood collection tube may include a composition volume of about 0.05 ml to about 1 ml. The blood collection tube may include a composition volume of about 0.20 ml to about 0.90 ml. The blood collection tube may include about 0.20 ml to about 0.30 ml of composition for a blood draw volume of about 8 ml to about 10 ml. The blood collection tube may include about 0.60 ml to about 0.90 ml of composition for a blood draw volume of about 4 ml to about 6 ml.

The blood sample collection tubes may be used for the stabilization and preservation of one or more of the following: proteins (e.g., prions), enzymes, antibodies, and biological materials that may or may not contain nucleic acids, including those with and without post-translational modifications. For example, the tubes may collect samples for analysis by one or more of the following: surface flow cytometry, intracellular cytometry, ELISA-based assays, and mass spectrometry. The blood sample collection tubes may be used for the stabilization and preservation of extracellular vesicles, exosomes, ectosomes, and/or microvesicles. The blood sample collection tubes may be used for the stabilization and preservation of viruses. This may include viral inactivation and viral load quantification. The virus may include any of the following: DNA/RNA, stranded/double stranded, and enveloped/non-enveloped. The blood sample collection tubes may be used for the stabilization and preservation of microorganisms such as bacteria, molds, and yeasts. The blood sample collection tubes may be used for the stabilization and preservation of extracellular parasites and/or intracellular parasites. The blood sample collection tubes may be used for the stabilization and preservation of exosomes, circulating tumor cells, other rare circulating cells, and tumor DNA.

The composition may be suitable for storing a blood sample for a period of at least about 3 days. The composition may be suitable for storing a blood sample for a period of at least about 7 days. The composition may be suitable for storing a blood sample for a period of at least about 14 days. The composition may be suitable for storing a blood sample for a period of at least about 30 days. The composition may be suitable for storing a blood sample for a period of at least about 60 days. The composition may be suitable for storing a blood sample for a period of at least about 90 days.

Synergism Between Components of Compositions of the Disclosure

The relationship between the various components of compositions of the disclosure and their impact on various cells in the blood is complex. For stabilizing cfRNA, stabilization of both WBCs and RBCs is necessary because they each contain RNA that would contaminate the cell-free fraction. For example and without limitation, if too little of the component capable of releasing an aldehyde (e.g., IDU) is present in the composition there is no effect on stabilizing the WBC, but if there is too much of the component capable of releasing an aldehyde (e.g., IDU) then destabilization of the RBCs begins to occur. α-cyclodextrin is helpful in stabilizing the WBCs but can damage the RBCs.

Accordingly, it is disclosed herein that various components of the compositions of the disclosure produce synergistic effects with respect to the stabilization of, e.g., nucleic acid in a cell. Accordingly, in any of the aspects embodiments of the disclosure, a polymer and a component capable of releasing an aldehyde, provide synergistic effects with respect to stabilization of, e.g., nucleic acid in a cell. Thus, in some embodiments, α-cyclodextrin and IDU act synergistically to stabilize, e.g., nucleic acid in a cell. In further embodiments, α-cyclodextrin and DU act synergistically to stabilize, e.g., nucleic acid in a cell. In some embodiments, PEG and IDU act synergistically to stabilize, e.g., nucleic acid in a cell. In still further embodiments, PEG and DU act synergistically to stabilize, e.g., nucleic acid in a cell.

Compositions of the disclosure facilitate stabilization of cfRNA, cfDNA, proteins and other cellular matter located within extracellular vesicles, genomic DNA and RNA and other RNA species (e.g., mRNA, miRNA, piRNA, siRNA, shRNA and others), allowing for downstream isolation and testing of both cell free and cellular matter (e.g., DNA and RNA from within white blood cells, circulating tumor cells (CTCs), circulating fetal cells, or other rare circulating cells). In further embodiments, the compositions of the disclosure are useful for direct and indirect extracellular vesicle analysis.

In some embodiments, the cell is a blood cell. In further embodiments, the blood cell is a white blood cell (WBC) or a red blood cell (RBC). In some embodiments, the component capable of releasing an aldehyde is diazolidinyl urea, imidazolidinyl urea, 1,3,5-tris(hydroxyethyl)-s-triazine, oxazolidine, 1,3-bis(hydroxymethyl)-5,5-dimethylimidazolidine-2,4-dione, quaternium-15, DMDM hydantoin, 2-bromo-2-nitropropane-1,3-diol, 5-bromo-5-nitro-1,3-dioxane, tris(hydroxymethyl) nitromethane, hydroxymethylglycinate, polyquaternium, or a combination thereof. In any of the embodiments of the disclosure, the component capable of releasing an aldehyde is imidazolidinyl urea (IDU).

In some embodiments, the polymer is Polyethylene Glycol (PEG) (at various molecular weights that are understood in the art), Polyvinylpyrrolidone (PVP), Magnesium Gluconate, Methyl Cellulose (MC), Ethyl Cellulose (EC), Hydroxyethyl Cellulose (HEC), Hydroxypropyl Cellulose (HPC), Dextrin (at various molecular weights that are understood in the art), Dextran (at various molecular weights that are understood in the art), Polyethylene Oxide, Poly Ethyl Oxazoline, Ficoll (at various molecular weights that are understood in the art), α-Cyclodextrin, ß-Cyclodextrin, Y-Cyclodextrin, Gelatins, Sugars (for example and without limitation, sucrose, mannitol, lactose, or trehalose), Hydroxypropyl Methyl Cellulose, Hydroxyethyl Methyl Cellulose. In any of the embodiments of the disclosure, the polymer is α-cyclodextrin.

The concentrations/amounts of each component of the compositions of the disclosure are contemplated as follows. It is contemplated that the component capable of releasing an aldehyde (e.g., IDU or DU) is present in the composition at a concentration of from about 10% to about 40%. It is contemplated that the cyclodextrin or a functionalized derivative thereof (e.g., α-cyclodextrin or a functionalized derivative thereof) is present in the composition at a concentration of from about 0.75% to about 4%. Functionalized derivatives of cyclodextrin are known in the art (see, e.g., Hanessian et al., J. Org. Chem. 60(15): 4786-4797 (1995) and Zhou et al., Polymer Chemistry 1: 1552-1559 (2010), each of which is incorporated by reference herein in its entirety).

Regarding the anticoagulant, it is contemplated that a citrate-based anticoagulant (e.g., ACD-A, ACD-B, or CPDA) is present at a concentration of from about 0.75% to about 4%. It is contemplated that an anticoagulant that is not citrate-based (e.g., EDTA) is present in the composition at a concentration of from about 0.05% to about 2%.

As used herein, a concentration or amount of a given component is described in terms of the concentration or amount of the component that is in the composition prior to addition of a biological sample (e.g., blood). Accordingly, the concentration or amount of each component as described herein after the biological sample has been added is expected to be about 20-fold less. By way of example, the amount of IDU that is present in a composition within a container (e.g., a blood tube) prior to addition of a biological sample may be from about 10% to about 40% by volume. After addition of the biological sample, however, the concentration of IDU in the container is expected to be from about 0.5% to about 2% by volume. Thus, if the volume of the composition in the container prior to addition of the biological sample is 0.2 ml, then the amount of IDU in the container is from about 20 μl to about 80 μl; after the addition of the biological sample, the amount of IDU in the container is from about 1 μl to about 4 μl.

In any of the aspects or embodiments of the disclosure, components having the same or similar properties may be substituted for one another. For example, DU (or any component capable of releasing an aldehyde) may be substituted for IDU in any of the aspects or embodiments of the disclosure; an alternative sugar (e.g., sucrose, mannitol, lactose, or trehalose) may be substituted for dextrose in any of the aspects or embodiments of the disclosure.

EXAMPLES

The figures provided herein demonstrate test data that assists in identifying composition components for minimizing white blood cell lysis, minimizing erythrocyte lysis, and maintaining the stability of cell-free DNA, extracellular vesicles (and the RNA located therein), and proteins.

FIG. 1 is graph depicting change in erythrocyte MCV using various anticoagulants. An increase in erythrocyte mean cell volume demonstrates an increase (or an expectation of an increase) in erythrocyte cell lysis. The graph shows results at three different storage temperatures from three different donors. Thus, anticoagulants demonstrating the ability to maintain mean cell volume so that it remains similar to mean cell volume at sample collection are preferred.

Figure 2:
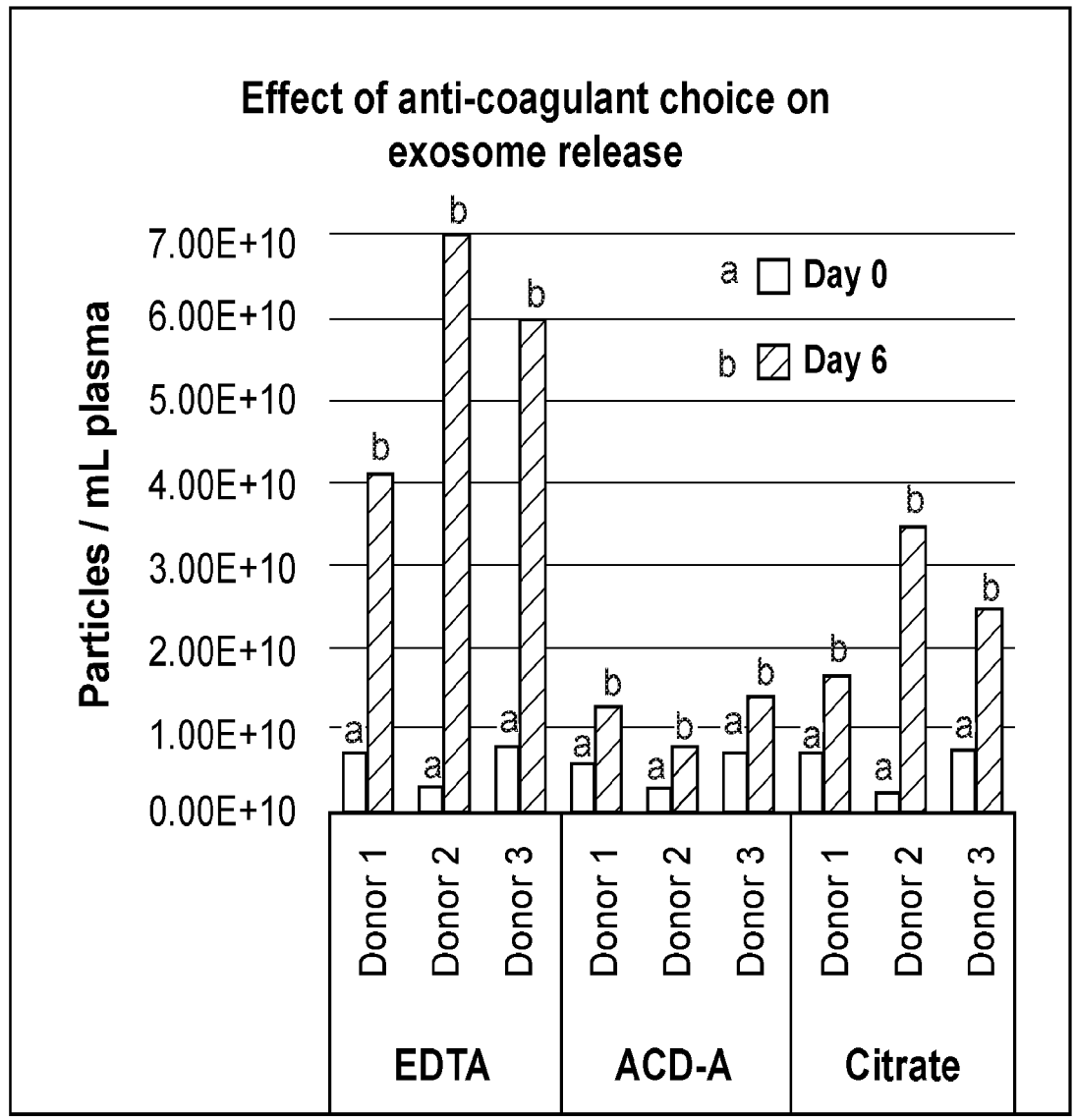
FIG. 2 is a graph depicting exosome release during use of various anticoagulants.

FIG. 2 is a graph depicting exosome release during use of various anticoagulants. Similar to the release of genomic DNA, the release of extracellular vesicles can create challenges in the effective isolation of RNA. As a result, an anticoagulant that maintains exosome release so that it is similar to that at the time of sample collection is preferred.

Figure 3:
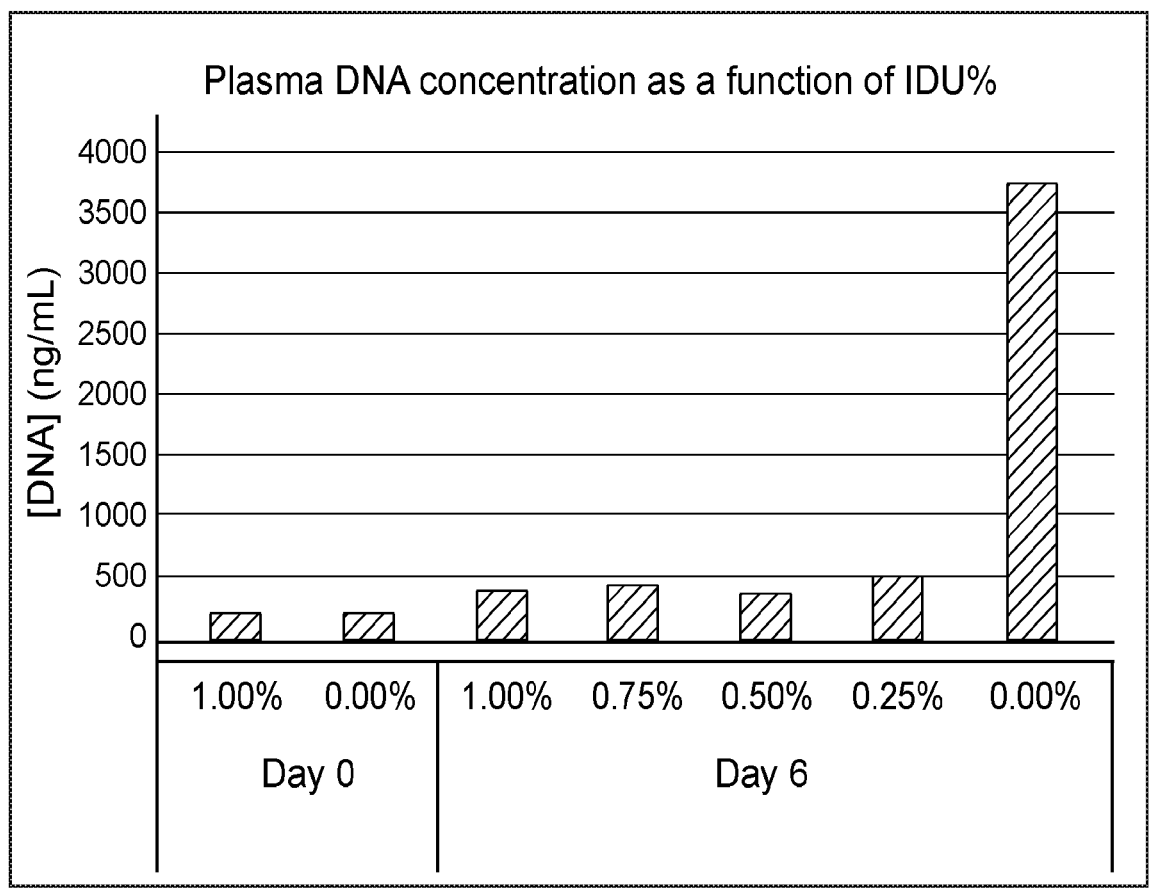
FIG. 3 is a graph depicting plasma DNA concentration as a function of the percentage of preservative.

FIG. 3 is a graph depicting plasma DNA concentration as a function of the percentage of preservative. An increase in the DNA concentration demonstrates an increase in the amount of genomic DNA and thus represents an increase in white blood cell lysis. Thus, a desirable amount of preservative maintains DNA concentration while avoiding over preservation and crosslinking which may damage DNA, extracellular vesicles, or proteins.

Figure 4A:
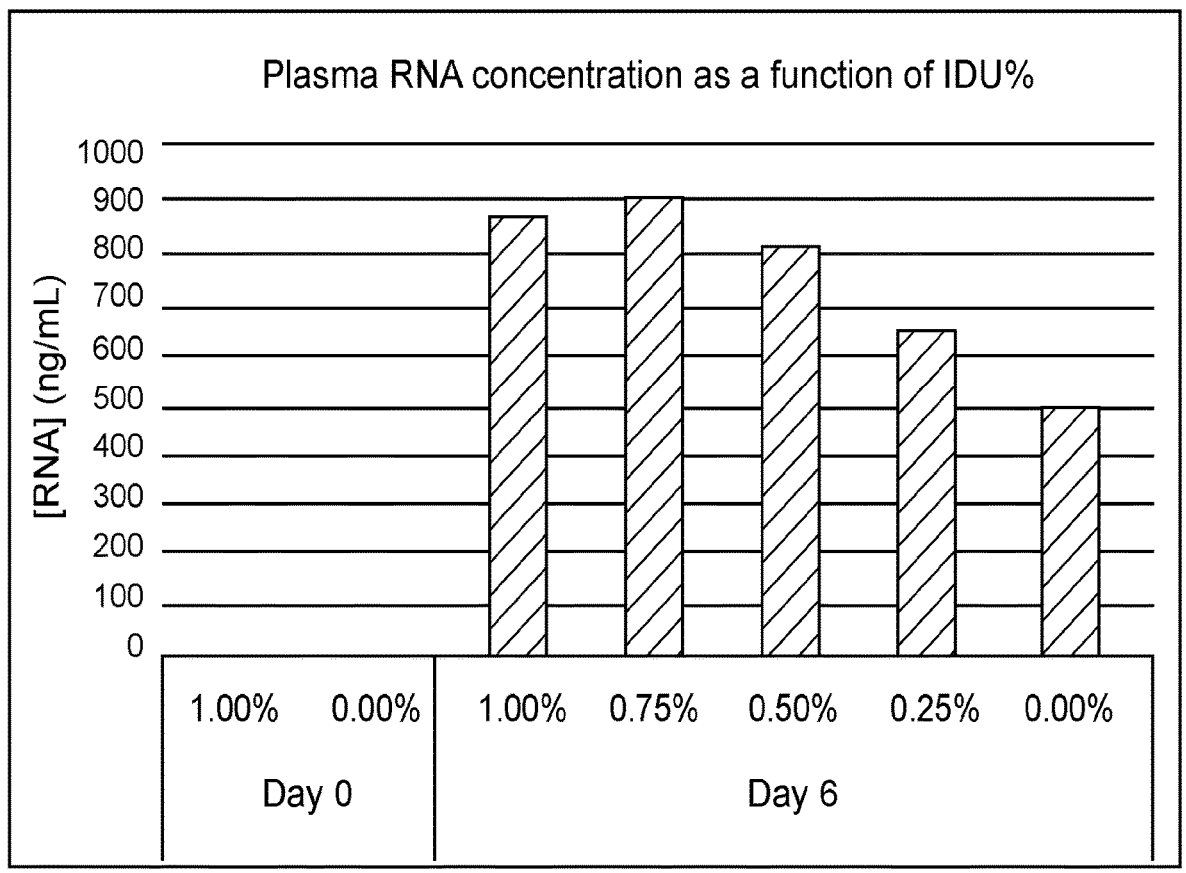
FIG. 4A is a graph depicting plasma RNA concentration as a function of the percentage of preservative.

FIG. 4A is a graph depicting plasma RNA concentration as a function of the percentage of preservative. An increase in the RNA concentration demonstrates an increase in the amount of released exosome. Thus, a desirable amount of preservative maintains RNA concentration while avoiding over preservation and crosslinking which may damage DNA, extracellular vesicles, or proteins.

Figure 4B:
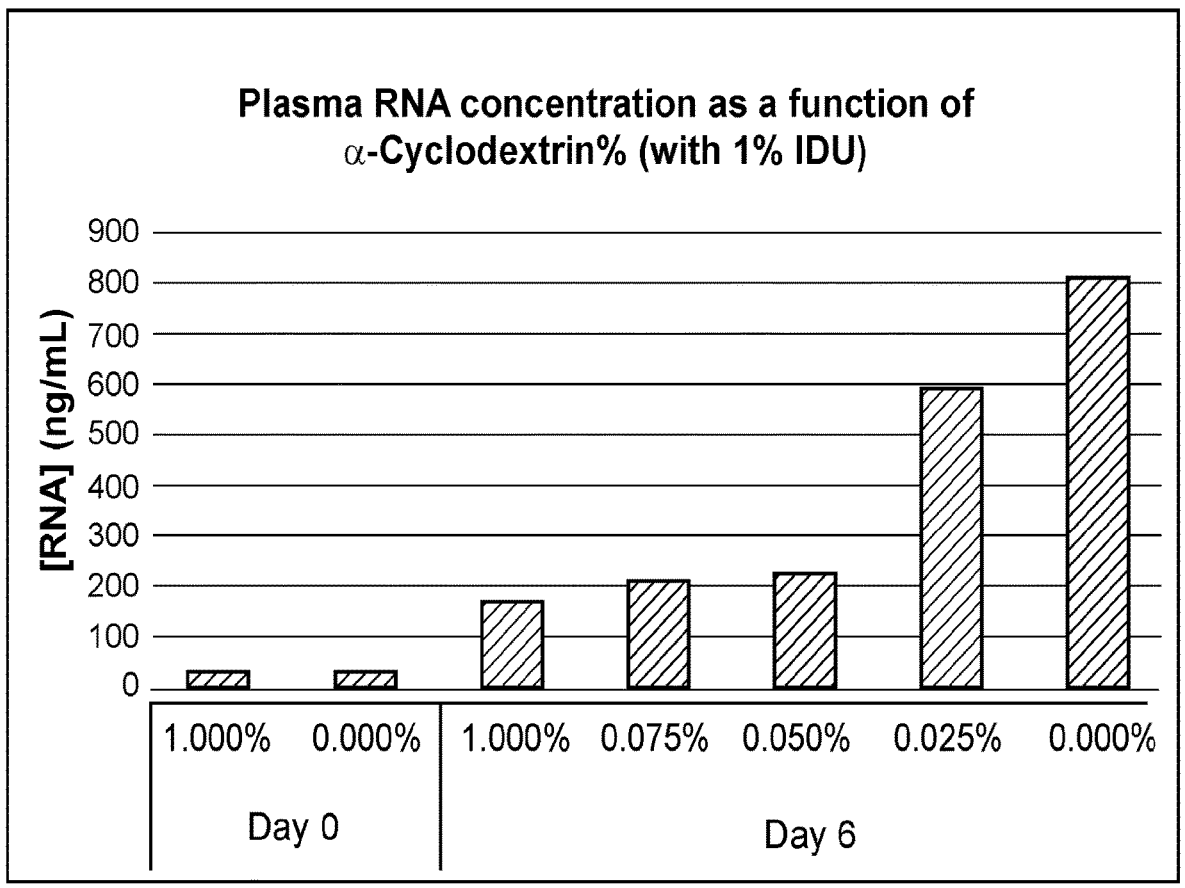
FIG. 4B is a graph depicting plasma RNA concentration as a function of the percentage of α-cyclodextrin.

FIG. 4B is a graph depicting plasma RNA concentration as a function of the percentage of α-cyclodextrin. An increase in the RNA concentration demonstrates an increase in the amount of released exosome. Thus, a desirable amount of polysaccharide maintains RNA concentration while avoiding hemolysis.

Figure 5A:
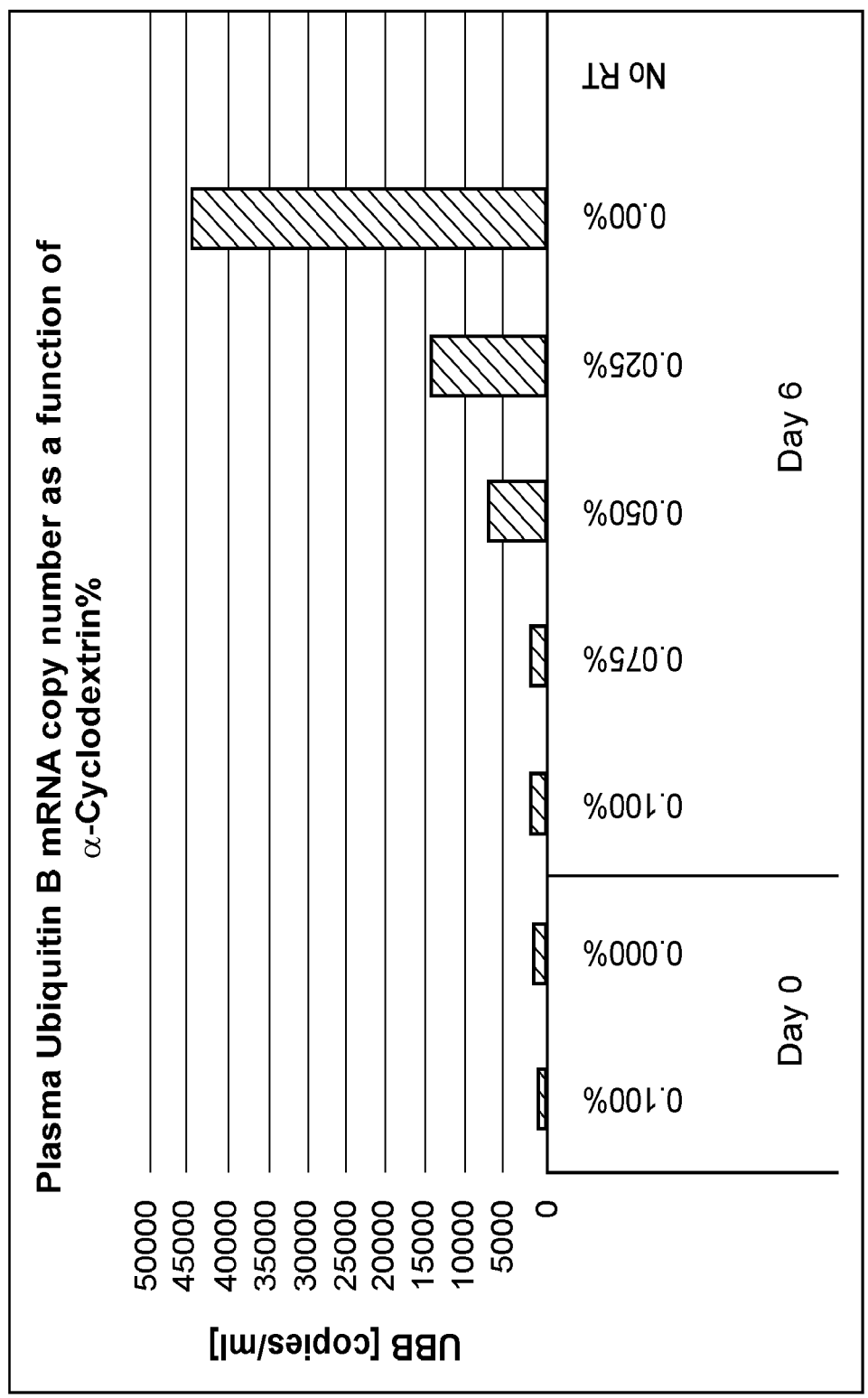
FIG. 5A is a graph depicting ubiquitin B mRNA copy number as a function of the percentage of α-cyclodextrin.

FIG. 5A is a graph depicting ubiquitin B mRNA copy number as a function of the percentage of α-cyclodextrin. An increase in the RNA concentration demonstrates an increase in the amount of released exosome. Thus, a desirable amount of polysaccharide maintains RNA concentration while avoiding hemolysis.

Figure 5B:
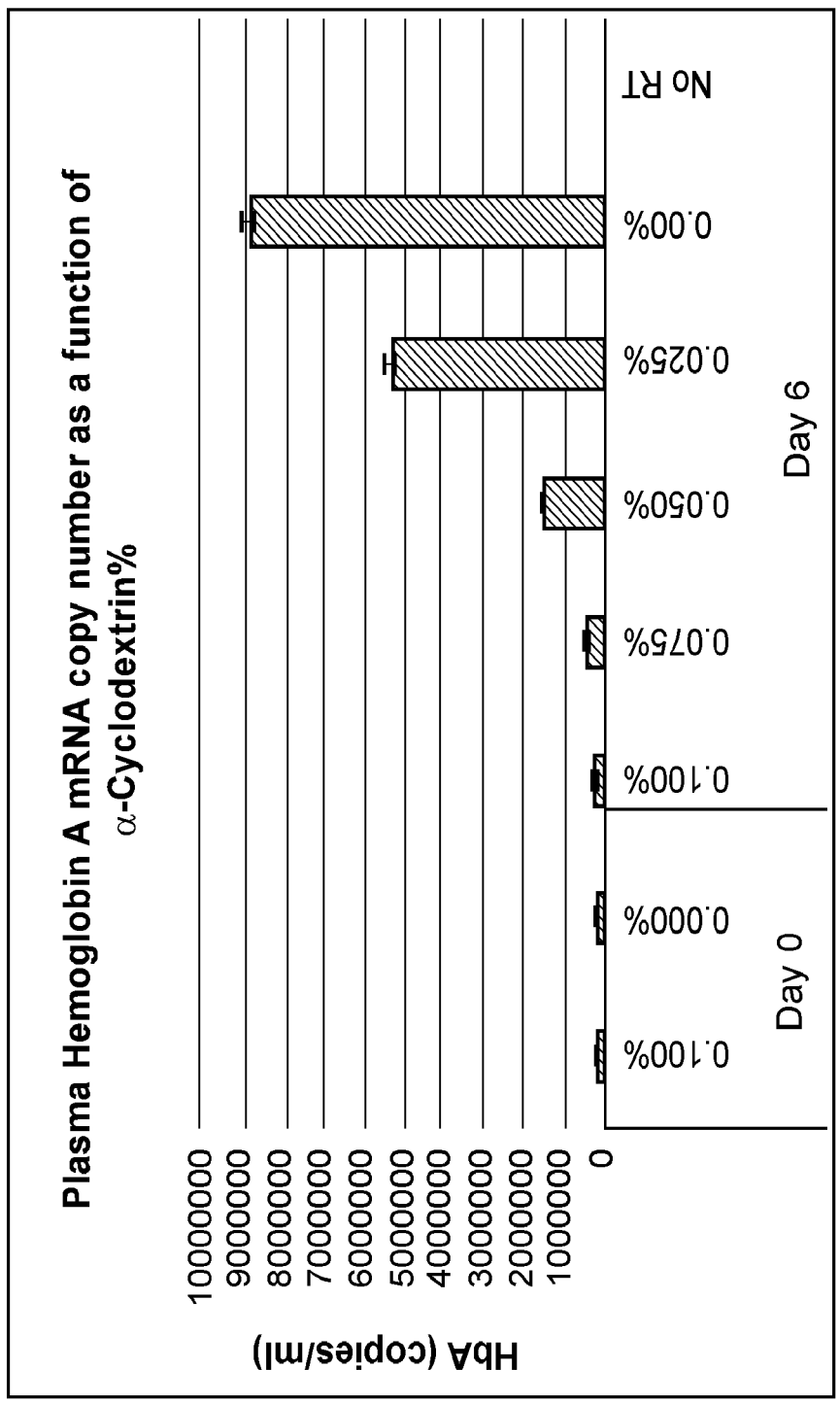
FIG. 5B is a graph depicting hemoglobin A mRNA copy number as a function of the percentage of α-cyclodextrin.

FIG. 5B is a graph depicting hemoglobin A mRNA copy number as a function of the percentage of α-cyclodextrin. An increase in the RNA concentration demonstrates an increase in the amount of released exosome. Thus, a desirable amount of polysaccharide maintains RNA concentration while avoiding hemolysis.

Synergistic Effects of Components of Compositions of the Disclosure

Figure 7:
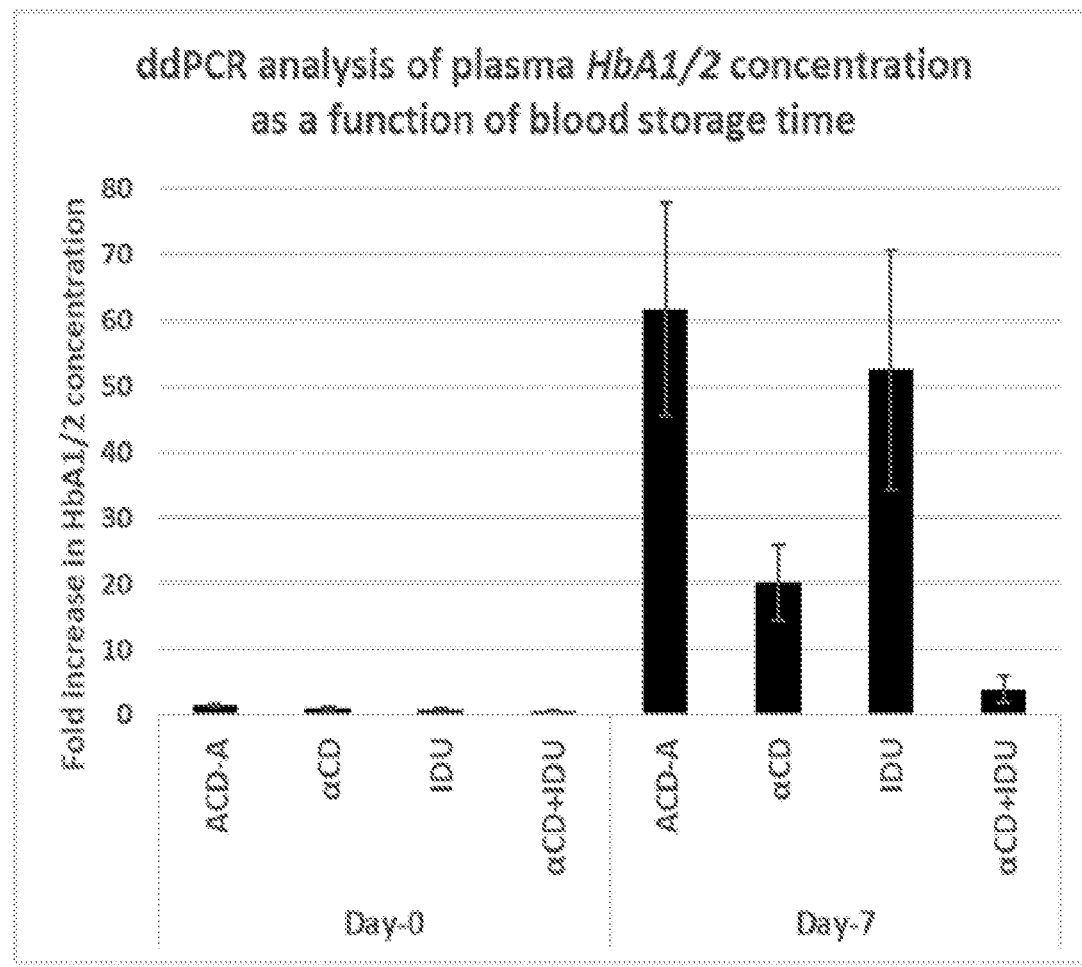
FIG. 7 shows the fold increase in concentration of red blood cell-specific (RBC-specific) transcript Globin A1/2 as a function of whole blood storage time. cfRNA was isolated as indicated in the description of FIG. 6 and herein below, reverse transcribed (Bio-Rad iScript), and used in droplet digital PCR reactions (Bio-Rad QX200 set-up) with commercially available primer/probes (Thermo-Fisher). Results are the mean with standard deviation from 3 healthy donors.
Figure 8:
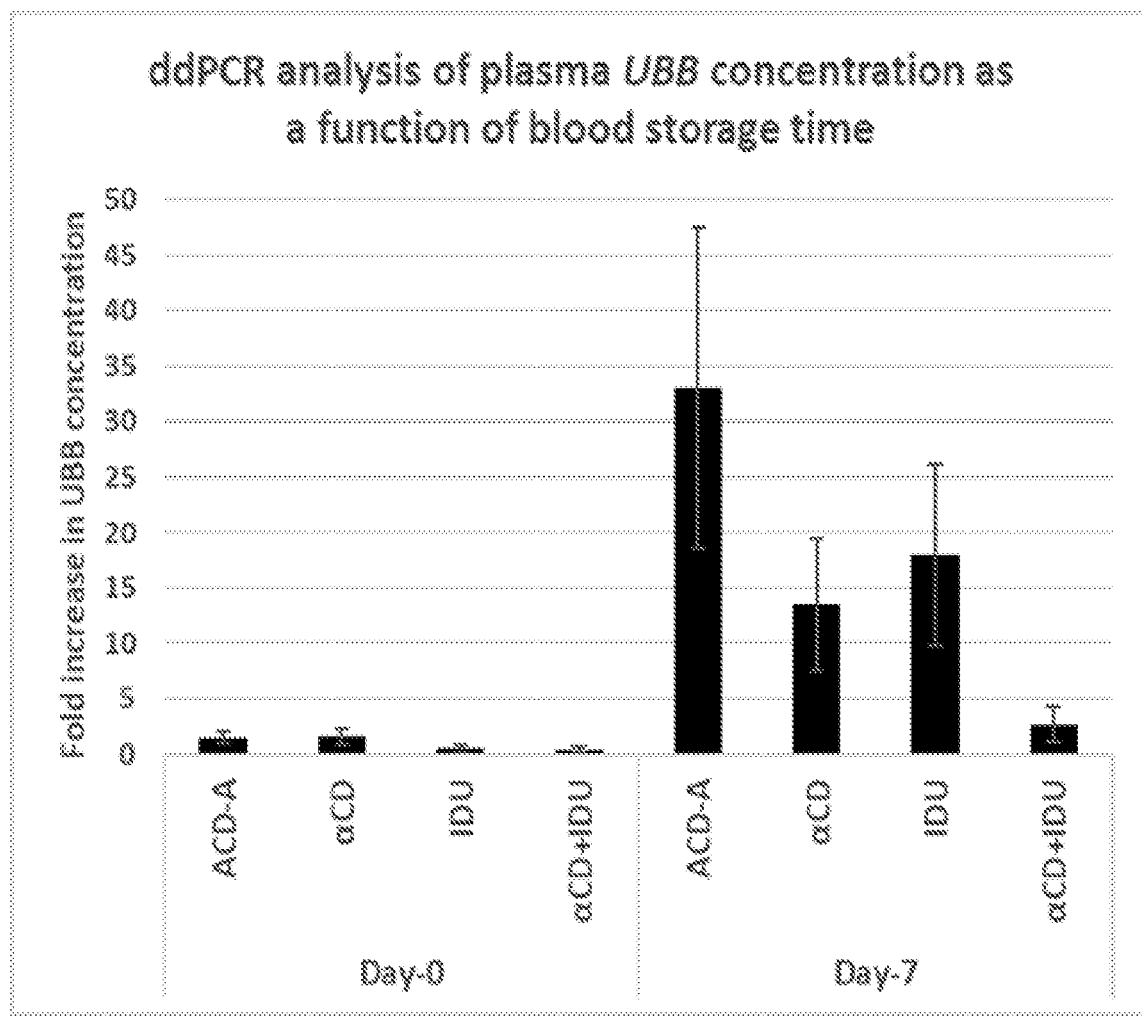
FIG. 8 shows the fold increase in concentration of Ubiquitin B transcript (expressed by all cells) as a function of whole blood storage time. cfRNA was isolated as indicated in the description of FIG. 6 and herein below, reverse transcribed (Bio-Rad iScript), and used in droplet digital PCR reactions (Bio-Rad QX200 set-up) with commercially available primer/probes (Thermo-Fisher). Results are the mean with standard deviation from 3 healthy donors.

The working hypothesis for the container (e.g., blood collection tube) that comprises a composition of the disclosure was that cell-free RNA (cfRNA), including messenger RNA, micro-RNA, non-coding RNA, etc., is stable in blood plasma via encapsulation within extracellular vesicles (EVs). Thus, because aspects of the disclosure are directed to stabilizing draw-time concentrations of cfRNA, the goal was to maintain the initial concentration of EVs. The experiments depicted in FIGS. 6, 7, and 8 demonstrated that the RNAx BCT stabilized draw-time concentrations of EVs and associated cfRNA for up to 7 days post blood draw. In the experiments, the functional components of the RNAx BCT are the preservatives imidazolidinyl urea (IDU) and α-cyclodextrin. The experiments were designed to test whether each of the foregoing components acted singly (additive effect) or whether the combination provided an unexpected, more pronounced outcome (synergistic effect). As discussed below and as shown in FIGS. 6-8, the combination showed an unexpected synergistic effect.

On the background of the basal anti-coagulant, ACD-A, each of the preservatives (i.e., IDU and α-cyclodextrin) was added singly (at the same concentration utilized in the RNAx BCT) or together. Samples were collected into each formulation-containing tube and plasma was isolated either immediately (Day-0) or after seven days of storage at room temperature (Day-7). Cell-free RNA was purified from plasma samples using the commercial QIAamp Circulating Nucleic Acid Isolation Kit with an on-column DNase1 digest, all according to the manufacturer's recommendations (Qiagen). Purified cfRNA was then used in fluorometric analysis for total cfRNA as per manufacturer's recommendation (Qubit HS RNA Assay, Thermo-Fisher) or in droplet digital PCR (ddPCR, Bio-Rad QX200 workflow) using commercially available primer/probe sets for transcript-specific RNA expression.

Figure 6:
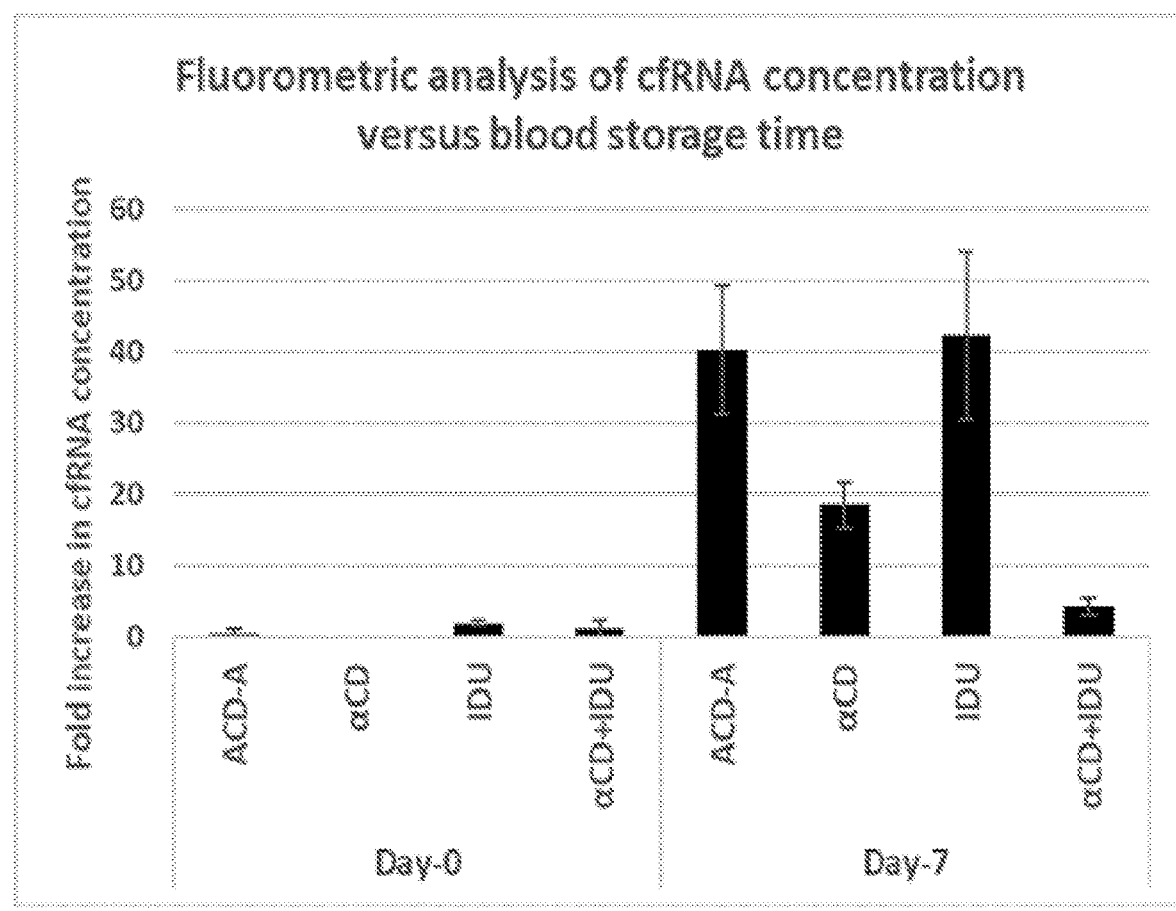
FIG. 6 shows the total cell-free RNA (cfRNA) concentration as a function of whole blood storage time. Plasma was isolated and cfRNA extracted using a commercially available kit (Qiagen, QIAamp Circulating Nucleic Acid Isolation Kit). Resultant cfRNA was quantified using the Qubit RNA HS Assay (Invitrogen). Results are the mean with standard deviation from 3 healthy donors.

As shown in FIG. 6, total cfRNA as measured by fluorometric analysis increased almost 60-fold over the course of 7 days in the non-stabilized ACD-A samples (n=3 independent donors). Addition of IDU by itself did not prevent the increases in cfRNA whereas α-cyclodextrin alone did limit increases in levels of cfRNA. However, the combination of IDU and α-cyclodextrin together significantly blunted increases in total cfRNA levels (increases of only 2-4 fold were observed).

To determine potential preference of the IDU or α-cyclodextrin preservatives for different cellular populations, ddPCR was utilized to determine transcript-specific changes in cfRNA levels. Hemoglobin alpha 1 and alpha 2 (HbA1/2) are expressed by erythrocytes and total levels of these transcripts mirrored that of total cfRNA (FIG. 7). This was expected, given that globin transcripts are the predominant transcripts found in blood plasma. Levels of Ubiquitin B, a gene expressed by all cells, was then determined. An effect for IDU was observed by itself in this regard; however, the combination of both IDU and α-cyclodextrin was necessary for the near complete stabilization of Ubiquitin B concentration (FIG. 8).

Altogether, these data demonstrated an unexpected synergistic effect between the component capable of releasing an aldehyde (e.g., IDU) and α-cyclodextrin in stabilizing draw-time concentration of cfRNA.

As used herein, unless otherwise stated, the teachings envision that any member of a genus (list) may be excluded from the genus; and/or any member of a Markush grouping may be excluded from the grouping.

Unless otherwise stated, any numerical values recited herein include all values from the lower value to the upper value in increments of one unit provided that there is a separation of at least 2 units between any lower value and any higher value. As an example, if it is stated that the amount of a component, a property, or a value of a process variable such as, for example, temperature, pressure, time and the like is, for example, from 1 to 90, preferably from 20 to 80, more preferably from 30 to 70, it is intended that intermediate range values such as (for example, 15 to 85, 22 to 68, 43 to 51, 30 to 32 etc.) are within the teachings of this specification. Likewise, individual intermediate values are also within the present teachings. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the comparative teaching of amounts expressed as weight/volume percent for two or more ingredients also encompasses relative weight proportions of the two or more ingredients to each other, even if not expressly stated. For example, if a teaching recites 2% A, and 5% B, then the teaching also encompasses a weight ratio of A:B of 2:5. Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes.

The term "consisting essentially of to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of (namely, the presence of any additional elements, ingredients, components or steps, does not materially affect the properties and/or benefits derived from the teachings; or even consist of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps. All references herein to elements or metals belonging to a certain Group refer to the Periodic Table of the Elements published and copyrighted by CRC Press, Inc., 1989. Any reference to the Group or Groups shall be to the Group or Groups as reflected in this Periodic Table of the Elements using the IUPAC system for numbering groups.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

What is claimed is:

1. A composition comprising:
   (i) a component capable of releasing an aldehyde;
   (ii) an anticoagulant comprising citric acid, trisodium citrate, and dextrose; and
   (iii) α-cyclodextrin,
   wherein the component capable of releasing an aldehyde is imidazolidinyl urea.

2. The composition of claim 1, wherein the anticoagulant is anticoagulant citrate dextrose-A (ACD-A), anticoagulant citrate dextrose-B (ACD-B), or citrate-phosphate-dextrose-adenine (CPDA).

3. The composition of claim 1, wherein the dextrose is present at a concentration of from about 2% to about 20% (weight/volume).

4. The composition of claim 3, wherein citrate ion concentration is from about 200 mM to about 500 mM.

5. The composition of claim 1, wherein the citric acid is present at a concentration of from about 0.5% to about 4% (weight/volume).

6. The composition of claim 5, wherein the trisodium citrate is present at a concentration of from about 3% to about 15% (weight/volume).

7. The composition of claim 1, wherein the component capable of releasing an aldehyde is present at a concentration of from about 10% to about 40% (weight/volume).

8. The composition of claim 1, wherein the α-cyclodextrin is present at a concentration of from about 0.75% to about 4%.

9. A method of treating a single blood sample with the composition of claim 1, comprising contacting the sample with the composition and isolating one or more of DNA, RNA, extracellular vesicles, circulating tumor cells, circulating rare cells, or proteins from the sample.

10. A method of inhibiting lysis of a cell comprising contacting the cell with a composition of claim 1, wherein the inhibiting prevents release of nucleic acid and/or an extracellular vesicle from the cell.

11. The method of claim 10, wherein the cell is a white blood cell.

12. The method of claim 10, wherein the cell is a red blood cell.

13. The method of claim 10, wherein the nucleic acid is cell free RNA (cfRNA), cell free DNA (cfDNA), cellular RNA, or cellular DNA.

14. The method of claim 10, wherein lysis is inhibited for at least about 24 hours.

15. The method of claim 14, wherein lysis is inhibited by at least 2 days, or at least 3 days, or at least 4 days.

16. The method of claim 10, further comprising maintaining the cell for at least about 24 hours and then isolating the nucleic acid from the cell.

17. The method of claim 16, wherein the cell is maintained at room temperature.

\* \* \* \* \*